(12) United States Patent
Forbes

(10) Patent No.: US 9,767,470 B2
(45) Date of Patent: Sep. 19, 2017

(54) EMOTIONAL SURVEY

(71) Applicant: David Lowry Forbes, Lincoln, MA (US)

(72) Inventor: David Lowry Forbes, Lincoln, MA (US)

(73) Assignee: Forbes Consulting Group, LLC, Lexington, MA (US)

( * ) Notice: Subject to any disclaimer, the term of this patent is extended or adjusted under 35 U.S.C. 154(b) by 0 days.

(21) Appl. No.: 13/683,729

(22) Filed: Nov. 21, 2012

(65) Prior Publication Data

US 2013/0085808 A1    Apr. 4, 2013

Related U.S. Application Data

(63) Continuation-in-part of application No. 12/872,531, filed on Aug. 31, 2010, now Pat. No. 9,558,499, and a continuation-in-part of application No. 12/713,539, filed on Feb. 26, 2010, now Pat. No. 9,603,564.

(51) Int. Cl.
*G06Q 30/02*   (2012.01)
*G06F 19/00*   (2011.01)

(52) U.S. Cl.
CPC ......... *G06Q 30/0203* (2013.01); *G06Q 30/02* (2013.01); *G06Q 30/0201* (2013.01); *G06F 19/345* (2013.01); *G06F 19/363* (2013.01)

(58) Field of Classification Search
CPC ............... G06Q 30/02; G06Q 30/0203; G06Q 30/0201; G06Q 30/0242; G06Q 30/0204; A61B 5/165; A61B 5/16; A61B 5/162; A61B 5/0484; A61B 5/04842; A61B 5/164; A61B 5/167; A61B 3/113; G06F 19/345; G06F 19/3443; G06F 17/27; G06F 17/30032; G06F 19/3406; G09B 7/00; G09B 19/00; G09B 23/28; G06K 9/00308; G06K 9/00302; G06K 9/00315; G06K 9/00335; G06K 9/00221; H04N 21/44218; H04N 5/23219
USPC ......................................................... 434/236
See application file for complete search history.

(56) References Cited

U.S. PATENT DOCUMENTS

| | | | |
|---|---|---|---|
| 6,292,688 | B1 | 9/2001 | Patton |
| 6,826,540 | B1 | 11/2004 | Plantec et al. |
| 7,606,726 | B2 | 10/2009 | Nelson |
| 7,720,784 | B1 | 5/2010 | Froloff |
| 7,942,816 | B2 | 5/2011 | Satoh et al. |

(Continued)

FOREIGN PATENT DOCUMENTS

| | | |
|---|---|---|
| CN | 1516561 | 7/2004 |
| CN | 1739451 | 3/2006 |

(Continued)

OTHER PUBLICATIONS

Cunningham, William A., et al., "The iterative reprocessing model: a multilevel framework for attitudes and evaluation", Social Cognition, vol. 25, No. 5, pp. 736-760, 2007 (25 pages).

(Continued)

*Primary Examiner* — Nathan Hillery
(74) *Attorney, Agent, or Firm* — Fish & Richardson P.C.

(57) ABSTRACT

A method includes presenting a media item to a test subject, the media item associated with a brand or product; presenting a series of sensory stimuli to the test subject; and, based on responses of the test subject to the series of stimuli, generating results suitable to inform a business decision related to marketing of the brand or product.

28 Claims, 24 Drawing Sheets

(56) References Cited

U.S. PATENT DOCUMENTS

| | | |
|---|---|---|
| 2003/0182123 A1 | 9/2003 | Mitsuyoshi |
| 2004/0082862 A1 | 4/2004 | Chance |
| 2004/0210159 A1 | 10/2004 | Kibar |
| 2005/0054904 A1 | 3/2005 | El-Nokaly |
| 2005/0062888 A1 | 3/2005 | Wood et al. |
| 2005/0209709 A1 | 9/2005 | Bradshaw |
| 2006/0153531 A1 | 7/2006 | Kanegae et al. |
| 2006/0229505 A1 | 10/2006 | Mundt |
| 2007/0050151 A1 | 3/2007 | Satoh |
| 2007/0066916 A1 | 3/2007 | Lemos |
| 2008/0037841 A1 | 2/2008 | Ogawa |
| 2008/0065468 A1 | 3/2008 | Berg et al. |
| 2008/0097235 A1 | 4/2008 | Ofek et al. |
| 2008/0101660 A1 | 5/2008 | Seo |
| 2008/0144882 A1 | 6/2008 | Leinbach et al. |
| 2008/0255949 A1 | 10/2008 | Genco |
| 2009/0024049 A1 | 1/2009 | Pradeep et al. |
| 2009/0083118 A1 | 3/2009 | Kallery et al. |
| 2009/0275006 A1 | 11/2009 | Cvencek |
| 2009/0285456 A1 | 11/2009 | Moon et al. |
| 2010/0009325 A1 | 1/2010 | Afanasiev et al. |
| 2010/0010317 A1 | 1/2010 | De Lemos |
| 2010/0055658 A1 | 3/2010 | Sturm et al. |
| 2010/0145215 A1 | 6/2010 | Pradeep |
| 2010/0179950 A1 | 7/2010 | Willcock |
| 2010/0221687 A1 | 9/2010 | Forbes |
| 2010/0266213 A1 | 10/2010 | Hill |
| 2011/0020778 A1 | 1/2011 | Forbes |
| 2011/0161011 A1 | 6/2011 | Hasson |
| 2012/0035428 A1 | 2/2012 | Roberts et al. |
| 2012/0071785 A1 | 3/2012 | Forbes |
| 2013/0185141 A1 | 7/2013 | Pradeep |

FOREIGN PATENT DOCUMENTS

| | | |
|---|---|---|
| CN | 103262143 A | 8/2013 |
| EP | 2401733 | 1/2012 |
| EP | 2612312 | 7/2013 |
| IN | 1666/CHENP2013 | 11/2014 |
| RU | 2166280 C2 | 5/2001 |
| RU | 2289310 C2 | 12/2006 |
| RU | 2013114331 | 10/2014 |
| RU | 2595964 C2 | 8/2016 |
| WO | WO 2007/0106083 | 9/2007 |
| WO | WO 2007/106518 | 9/2007 |
| WO | WO2008/023260 | 2/2008 |
| WO | WO2010/099443 | 9/2010 |
| WO | WO 2012/030652 | 3/2012 |
| WO | WO 2013/055535 | 4/2013 |
| WO | WO2014/081805 | 5/2014 |

OTHER PUBLICATIONS

Cunningham, William A., et al, "Attitudes to the Right—and Left: Frontal ERP Asymmetries Associated with Stimulus Valence and Processing Goals", ERP Asymmetries in Evaluation, NeuroImage, 28, pp. 827-834, 2005 (30 pages).

Scott, Lisa S., et al., "Electrophysiological Correlates of Facial Self-Recognition in Adults and Children", Cognition, Brain, Behavior, vol. IX(3), pp. 211-238, 2005 (28 pages).

Rudrauf, David, et al., "Enter feelings: Somatosensory responses following early stages of visual induction of emotion", International Journal of Psychophysiology, 72, pp. 13-23, 2009 (11 pages).

Grill-Spector, Kalanit, et al., "Visual Recognition: As soon as you know it is there, you know what it is", Psychological Science, Research Article, American Psychological Society, vol. 16, No. 2, 2005 (9 pages).

Luo, Qian, et al., "Neural dynamics for facial threat processing as revealed by gamma band synchronization using MEG", NIH Public Access, Author Manuscript, PMC Jan. 15, 2008, published Neuroimage, Jan. 15, 2007; 34(2): 839-847 (18 pages).

Rudrauf, David, et al., "Rapid Interactions between Venral Visual Stream and Emotion-Related Structures Rely on a Two-Pathway Architecture", The Journal of Neuroscience, Mar. 12, 2008, 28(11): pp. 2793-2803 (11 pages).

Damasio, Antonio, "Self Comes to Mind: Constructing the Conscious Brain", Pantheon Books, Random House, Inc., copyright 2010 (592 pages).

Cunningham, William A., et al., "Attitudes and evaluations: a social cognitive neuroscience perspective", Science Direct, www.sciencedirect.com 1364-6613/2007 Elsevier Ltd. All rights reserved. doi:10.1016/j.tics.2006.12.005, TRENDS in Cognitive Sciences, vol. 11, No. 3, pp. 97-104, specifically p. 102, Diagram Box 2, Feb. 7, 2007 (8 pages).

Office action from Australian Application No. 2010217803, dated May 3, 2013 (5 pages).

International Preliminary Report on Patentability for International Patent Application No. PCT/US2010/025588 dated Aug. 30, 2011 (8 pages).

International Search Report and Written Opinion for International Patent Application No. PCT/US2013/070966 dated Feb. 4, 2014 (13 pages).

Office action from Canadian Application No. 2753872 dated Sep. 12, 2013 (3 pages).

Extended European Search Report for EP application No. 10746912.4 dated Sep. 11, 2013 (8 pages).

Examination report from Australian Application No. 2011296331 dated May 3, 2013 (5 pages).

International Search Report and Written Opinion from PCT application No. PCT/US2012/57943 dated Jan. 7, 2013 (14 pages).

Schupp, Harald, T. et al., "The selective processing of emotional visual stimuli while detecting auditory targets: An ERP analysis", Brain Research 1230 (2008) pp. 168-176 (9 pages).

U.S. Appl. No. 12/713,539.

U.S. Appl. No. 12/872,531.

U.S. Appl. No. 13/249,968.

International Search Report and Written Opinion for International Patent Application No. PCT/US2010/025588 dated May 13, 2010 (10 pages).

International Search Report for PCT/US2011/049383 dated Dec. 29, 2011 (2 pages).

Transaction history and pending claims for U.S. Appl. No. 12/872,531.

Transaction history and pending claims for U.S. Appl. No. 12/713,539.

Response to Australian Office action filed on Aug. 1, 2014 for Australian application No. 2010217803 (48 pages).

Examination Report from Australian application No. 2010217803 dated Sep. 1, 2014 (7 pages).

Batty, M. et al.,"Early processing of the six basic facial emotional expressions", Cognitive Brain Research, 2003, vol. 17, pp. 613-620.

European Communication from European Application 11822401.3 dated May 4, 2015 (6 pages).

Communication for EP application No. 10746912.4 issued Sep. 27, 2013 (1 page).

Response to extended European Search Report for EP application No. 10746912.4 filed on Apr. 7, 2014 (10 pages).

Office action from Chinese application 201180051770.3 dated Jan. 7, 2015 (11 pages).

European communication for EP application 11822401.3 dated Apr. 25, 2013 (2 pages).

Chinese Office action with English translation from Chinese application 201180051770.3 dated Jan. 7, 2015 (26 pages).

International Preliminary Report on Patentability from PCT application PCT/US2012/057943 dated Apr. 10, 2014 (7 pages).

International Preliminary Report on Patentability from PCT application PCT/US2011/049383 dated Mar. 14, 2013 (9 pages).

International Search Report and Written Opinion from PCT application PCT/US2011/049383 dated Dec. 29, 2011 (7 pages).

International Preliminary Report on Patentability from PCT application PCT/US2010/025588 dated Aug. 30, 2011 (8 pages).

International Preliminary Report on Patentability from PCT application PCT/US2013/070966 dated Jun. 4, 2015 (7 pages).

(56) References Cited

OTHER PUBLICATIONS

Batty, Magali, et al., "Early processing of the six basic facial emotional expressions", Cognitive Brain Research 17, pp. 613-620, May 22, 2003 (8 pages).
Response to Examination report dated Sep. 12, 2013 in Canadian Application 2753872, filed on Mar. 12, 2014 (24 pages).
Examination Report from Canadian Application 2753872 dated Mar. 12, 2015 (4 pages).
Voluntary Amendment filed in Australian Application 2011296331 dated Mar. 12, 2013 (13 pages).
Examination Report from European Application 11822401.3 dated Apr. 17, 2015 (3 pages).
Office Action in Australian Application No. 2015200472, dated Mar. 2, 2016, (5 pages).
European Communication from European Application 10746912.4 dated May 31, 2016 (6 pages).
Office Action in Australian Application No. 2015200496, dated Mar. 8, 2016 (3 pages).
Chinese Office action with English translation from Chinese application 201180051770.3, dated Oct. 20, 2015, (19 pages).
Russian Decision on Grant for Application No. 2013114331/08(021174) dated Jun. 3, 2016 (16 pages).
Office action with English translation issued in Russian application No. 2013114331 dated Aug. 12, 2015 (10 pages).

|             | INTRAPSYCHIC | INSTRUMENTAL | INTERPERSONAL |
|-------------|--------------|--------------|---------------|
| EXPECTATIONS | Safe, Confident<br>SECURITY<br>Insecure, Afraid<br>202 | Free, Powerful<br>EMPOWERMENT<br>Trapped, Frustrated<br>204 | Accepted, Belonging<br>BELONGING<br>Isolated, Lonely<br>206 |
| EXPERIENCES | Unique, Interesting<br>IDENTITY<br>Ordinary, Boring<br>208 | Involved, Absorbed<br>ENGAGEMENT<br>Passive, Indifferent<br>210 | Sharing, Caring<br>NURTURANCE<br>Selfish, Unloved<br>212 |
| OUTCOMES    | Talented, Exceptional<br>MASTERY<br>Incompetent<br>214 | Victorious, Productive<br>ACHIEVEMENT<br>Defeated, Pointless<br>216 | Proud, Respected<br>ESTEEM<br>Ashamed, Disgraced<br>218 |

FIG. 7E

Based on this commercial, I worry that shopping at General's would leave me feeling a little bit...

Because shopping isn't always a perfect experience, next we'd like you to do the same exercise again, but this time using a different sentence:

Based on this commercial, I worry that shopping at General's would leave me feeling a little bit...

Again, this sentence will stay at the top of your screen as pictures appear very quickly. You won't really have time to "think" about your responses. Go with your "gut" feeling and if you feel an impulse to select a picture, go ahead and press the space bar.

For pictures that DON'T complete the sentence, do nothing and a different picture will appear. There are no wrong answers. You can pick as many or as few as you like.

Let's get started.

Based on this commercial, I worry that shopping at General's would leave me feeling a little bit...

718

EMOTIONAL SURVEY

CLAIM OF PRIORITY

This application is a continuation-in-part of U.S. application Ser. No. 12/872,531, filed on Aug. 31, 2010, which is a continuation-in-part of U.S. application Ser. No. 12/713,539, filed Feb. 26, 2010, which claims priority under 35 U.S.C. 119(e) to U.S. Provisional Application Ser. No. 61/156,236, filed Feb. 27, 2009, the entire contents of all of which are hereby incorporated by reference.

BACKGROUND

Many psychological tests exist that elicit and/or assess the reactions or responses of a person as the person is exposed to stimuli. Such techniques may involve, for example, presenting one or more images, questions, or ideas as stimuli to a test subject within the context of a particular topic of interest to a researcher. In response, the test subject provides feedback indicative of his emotional state as he reacts to viewing the images. If the test subject is given enough time to react to the stimuli, the feedback may include the effects of the test subject's cognitive processing of each stimulus. The feedback is analyzed according to one or more emotional and/or motivational theories to assess psychological characteristics of the test subject relevant to the topic of interest.

SUMMARY

Among other things, we describe an emotional survey (e.g., the accumulation and use of emotion data) that probes subconscious feelings and emotions that drive, for example, consumer behavior. The results of the emotional survey are valuable for informing business decisions in marketing, including advertising, branding, and product development.

In a general aspect, a method includes presenting, on a user interface of a computing device, a media item to a test subject, the media item associated with a brand or product. The method further includes presenting, on a user interface of a computing device, a series of sensory stimuli to the test subject. The method also includes, based on responses of the test subject to the series of sensory stimuli, generating, using an analysis module of a computing device, results suitable to inform a business decision related to marketing of the brand or product.

Embodiments may include one or more of the following.

Generating results includes generating a textual or graphical summary of the responses of the test subject to the series of sensory stimuli.

Generating results includes identifying an emotion associated with the media item.

Generating results includes generating a motivational profile of the test subject.

Generating results includes generating a recommendation related to marketing of the brand or product. In some cases, generating a recommendation includes identifying an emotion associated with the media item; and generating a recommendation for a marketing campaign based on the identified emotion.

Presenting the media item includes presenting the media item to a plurality of test subjects and presenting the series of sensory stimuli includes presenting the series of sensory stimuli to the plurality of test subjects. Generating results includes generating results based on responses of the plurality of test subjects to the series of sensory stimuli. In some cases, generating results includes generating results based on a subset of responses of the plurality of test subjects to the series of sensory stimuli. In some cases, generating results includes filtering the responses to obtain the subset of responses.

Presenting a media item includes presenting at least one of a text-based item, an image, and a video.

Presenting a media item includes presenting an expression of a subject or an idea.

Presenting a media item includes presenting at least one of an image of a product, an image associated with a brand, an advertisement, a video of a product, a video associated with a brand, a brand slogan, and a product slogan.

The method includes presenting a priming sentence.

Presenting a series of sensory stimuli includes presenting a series of images.

Presenting a series of sensory stimuli includes presenting each of at least some of the sensory stimuli for a predefined period of time. In some cases, the period of time is less than about one second.

The method includes receiving the responses of the test subject to the series of sensory stimuli. In some cases, receiving the responses includes receiving the response to each sensory stimulus within a predefined period of time after presentation of the sensory stimulus, such as less than about 250 milliseconds.

The response of the test subject to the each of the sensory stimuli is indicative of an emotion the test subject feels toward at least one of the sensory stimuli and the media item.

In another general aspect, a computer-implemented system includes a presentation module configured to present, on a user interface of a computing device, a media item to a test subject, the media item associated with a brand or product, and present, on a user interface of a computing device, a series of sensory stimuli to the test subject. The system further includes an analysis module configured to generate, based on responses of the test subject to the series of sensory stimuli, results suitable to inform a business decision related to marketing of the brand or product.

Embodiments may include one or more of the following.

The analysis module is configured to generate a textual or graphical summary of the responses of the test subject to the series of sensory stimuli.

The analysis module is configured to identify an emotion associated with the media item.

The analysis module is configured to generate a motivational profile of the test subject.

The analysis module is configured to generate a recommendation related to marketing of the brand or product. In some cases, the analysis module is configured to identify an emotion associated with the media item; and generate a recommendation for a marketing campaign based on the identified emotion.

The presentation module is configured to present the media item to a plurality of test subjects; and presenting the series of sensory stimuli includes presenting the series of sensory stimuli to the plurality of test subjects. The analysis module is configured to generate results based on responses of the plurality of test subjects to the series of sensory stimuli. In some cases, the analysis module is configured to generate results based on a subset of responses of the plurality of test subjects to the series of sensory stimuli. In some cases, the analysis module is configured to filter the responses to obtain the subset of responses.

The media item includes at least one of a text-based item, an image, and a video.

Presenting a media item includes presenting an expression of a subject or an idea.

The media item includes at least one of an image of a product, an image associated with a brand, an advertisement, a video of a product, a video associated with a brand, a brand slogan, and a product slogan.

The method includes presenting a priming sentence.

The series of sensory stimuli includes a series of images.

The presentation module is configured to present each of the sensory stimuli for a predefined period of time, such as less than about one second.

The system includes a communication module configured to receive the responses of the test subject to the series of sensory stimuli. In some cases, the communication module is configured to receive the response to each sensory stimulus within a predefined period of time after presentation of the sensory stimulus, such as less than about 250 milliseconds.

The response of the test subject to the each of the sensory stimuli is indicative of an emotion the test subject feels toward at least one of the sensory stimulus and the media item.

The systems and methods described here have advantages, including one or more of the following. For instance, the emotional survey described here can identify specific subconscious emotions driving consumer behavior, thus providing insights into the mindset of the consumer that are useful for driving marketing and other business decisions. Because the emotional survey elicits responses directly from the emotional features and functioning of the brain, the survey can provide data that would typically be inaccessible even with a direct in-person interview.

The survey techniques described here capture such emotional insight even in challenging situations. For instance, in cases where individuals are unable or unwilling to describe their feelings or do not know what their feelings are, the survey techniques described here are still able to elicit the subconscious emotions of those individuals. These survey techniques are well suited to generating new emotional insights into product categories with leading brands with a long history. In addition, the survey techniques are useful for starting conversations about emotions in topic areas where conversation may be difficult, such as conversations about sensitive health care topics.

The emotional survey described here can be administered quickly and can be added to other pre-existing survey instruments with a minimal addition of survey time. In addition, the survey is straightforward and affordable to administer and thus can be easily deployed to large numbers of globally dispersed respondents without the need for specialized sampling, recruiting, or hardware.

These and other aspects, features, and implementations, and combinations of them, can be expressed as methods, apparatus, systems, components, software products, business methods, means and steps for performing functions, and in other ways.

Other features and advantages will be apparent from the following description and from the claims.

DESCRIPTION

FIG. 2 is a diagram of example motivational domains.

FIGS. 7A-7J are screenshots of an example of an emotional survey.

An emotional survey probes feelings and emotions (e.g., subconscious feelings and emotions) that drive consumer behavior. The results of the emotional survey are valuable for informing business decisions in a marketing context, including advertising, branding, and product development.

In the emotional survey, a topic stimulus, such as a subject, an idea, an image of a product, an advertisement (e.g., a still, audio, or video advertisement), a brand slogan, or another marketing- or product-related topic stimulus, or a combination of any two or more of them, is presented to a test subject. An open-ended priming sentence is also presented to the test subject. A series of sensory stimuli (e.g., images) are then rapidly displayed to the test subject, and the test subject is instructed to respond affirmatively to each sensory stimulus that evokes an emotion that the test subject associates with the topic stimulus. The results of the emotional survey provide insights into the emotions elicited in the test subject by the topic stimulus. Those insights can be used to guide marketing decisions. Thus, three elements are taken into account in the analysis: the topic stimulus, the sensory stimuli, and the responses in which the subjects link one or more of the sensory stimuli with the topic stimulus.

For example, Anita may be asked to think about the task or experience of doing laundry (the topic stimulus) and given a priming sentence of "I wish there was a laundry product that helped me feel more . . . ". She then is presented with a series of emotionally evocative images (the sensory stimuli) and asked to select the images that give her the feeling that completes her priming sentence. She is then shown images such as a football game, a concert cellist, a family dinner, and a nurse taking care of a patient. If she links the football game and the family dinner to the priming sentence, inferences might be drawn about her feelings and emotions relative to her needs and wants in this life task (i.e., doing laundry).

Figure 1:
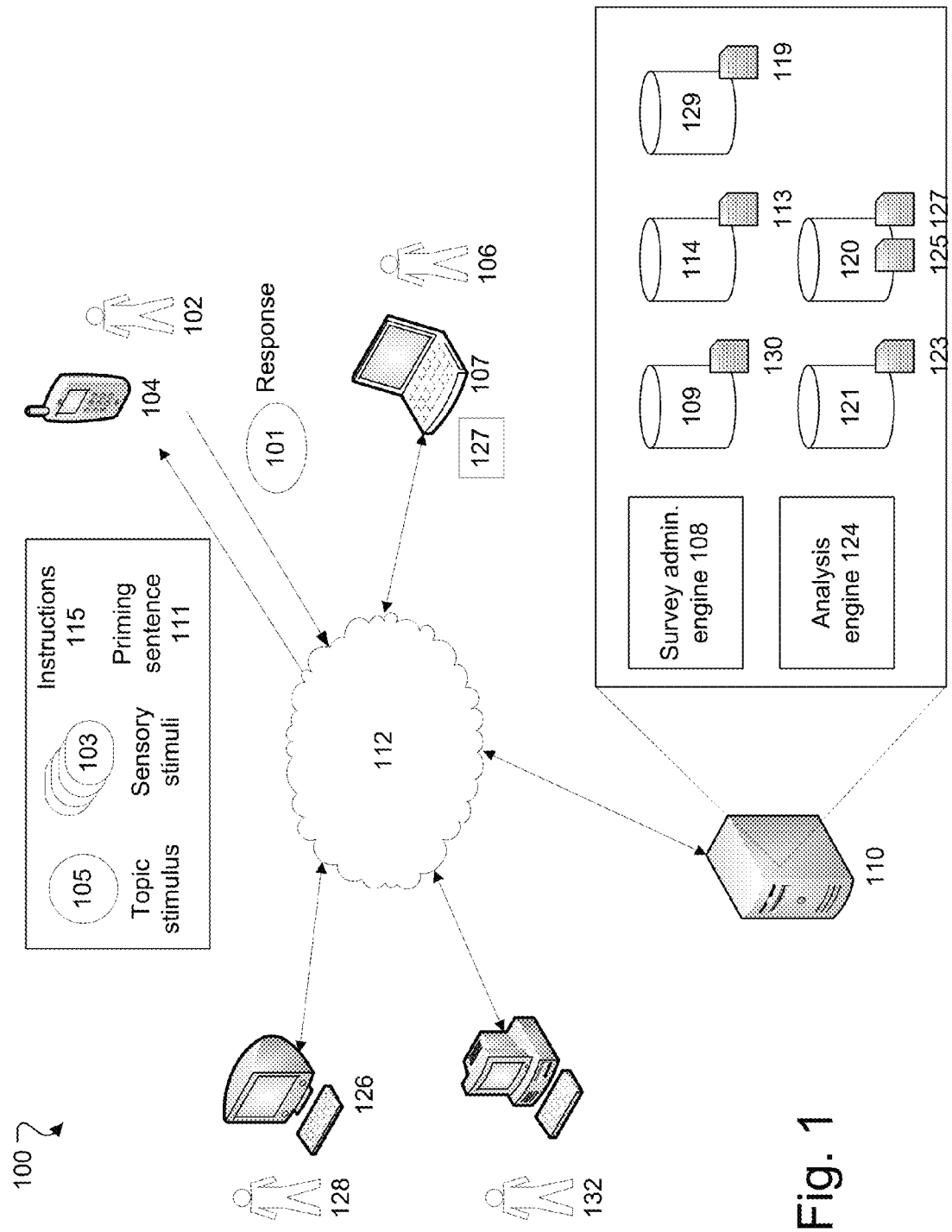
FIG. 1 is a block diagram of an example system for administering and analyzing the results of an emotional survey.

FIG. 1 is a block diagram of a system 100 for administering and analyzing an emotional survey that elicits emotional responses 101 to sensory stimuli 103 in the context of a topic stimulus 105 from a test subject 102. The responses 101 may be analyzed and used in a business context, e.g., to guide decisions related to marketing, such as advertising, branding, or product development. The responses may also be used in a non-business context, such as, e.g., a political context or a human resources context.

The emotional survey is presented to the test subject 102 on a display interface of a computing device 104, such as a computer or a mobile communication device (e.g., a smartphone or tablet). In some examples, the survey is self-administered by the test subject via the Internet or a mobile telephone network, e.g., in response to an email soliciting participants for the test or after scanning a quick response (QR) code printed on an advertisement.

In some examples, the survey is administered by a moderator 106, e.g., when the test is administered as part of a focus group or an in-person or telephone interview. The survey may be controlled via a computing device 107 operated by the moderator 106. For focus group administration of the survey, there may be multiple test subjects 102 each using a different computing device 104. For telephone administration of the survey, the survey is delivered to the test subject's computing device 104 via the Internet using a real-time messaging server (such as a Flash Media Server) to create a shared workspace in which the moderator and the test subject can interact. In some examples, one or more observers may watch the progress of the test subject's survey via an observer interface on a computing device operated by the observer.

A survey administration engine 108 administers the emotional survey to the test subject. The operation and sequencing of the activities of the survey administration engine can be controlled by the moderator 106 in the course of a survey, or can proceed automatically without human intervention. In the example of FIG. 1, the survey administration engine 108 is located on a server 110 and is accessed by the computing device 104 via the Internet 112. In some examples, the server is accessed via a mobile telephone network, such as a 3G or 4G network. In some examples, the survey administration engine 108 is a program stored on the computing device 104.

The survey administration engine 108 presents a topic stimulus 105 for the exercise. The topic stimulus is a media item, such as a text-based item, an image, a video, or another type of media item. The topic stimulus can be an idea (e.g., "Your experiences using laundry detergent," "Your feelings about the car you own," or "The process of buying a refrigerator") or a concrete stimulus, such as an image of a product, an advertisement (e.g., a still, audio, or video advertisement), a brand slogan, or another marketing- or product-related topic stimulus, to the test subject, and a combination of any two or more of them.

The survey administration engine 108 also presents a psychological priming sentence 111 to orient the test subject to the topic of focus for the survey. Thus, the survey has a topic, a topic stimulus that is related to the topic and is presented to the subject, and a priming sentence that is related to the topic and the topic stimulus and provides a transition to the sensory stimuli that then follow. The priming sentence may be a positive sentence (i.e., a motivator) or a negative sentence (i.e., an inhibitor). An example positive priming sentence is "Based on what I just read, I am excited to try product X because it seems that it would help me feel more _____." An example negative priming sentence is "Based on this advertisement, I am afraid that driving this car may make me feel_____." The topic stimulus and the priming sentence are stored in a survey configuration database 109 along with a configuration file 130 that defines how the survey is to be executed, as discussed in greater detail below.

After the topic stimulus and priming sentence are displayed, a series of sensory stimuli (e.g., stimulus images) each selected to evoke a corresponding emotion in the test subject is presented in rapid succession, e.g., for less than one second per image, as discussed in greater detail below. The images 113 are stored in an image stimulus database 114 located on the server 110 along with the survey administration engine 108. In some examples, the image database 114 is located on a different server or on the computing device 104.

Each sensory stimulus (e.g., each stimulus image) is chosen because it is known to be associated with one or more specific emotions, i.e., each image is known to elicit a particular emotional characteristic from a person viewing the image. In some examples, each image is classified according to a motivational model including a matrix of motives. In some examples, each image has been tested via randomized quantitative sampling to determine and/or confirm a correlation between the image and one of nine motivational domains.

Referring to FIG. 2, an example motivational matrix 200 represents a psychological model describing nine core aspirations of the test subject 102, arranged in two dimensions: a focus of aspiration (along the x axis) versus a level of aspiration (along the y axis). The focus of aspiration describes, e.g., areas in which the test subject is aspiring to improve his life. For example, an intra-psychic focus describes how the person feels about himself; an instrumental focus describes how the person feels about his activities; and an interpersonal focus describes how the person feels about his relationships with others. The level of aspiration describes, e.g., the desired emotional state of the test subject as he fulfills his aspirations. For example, "expectations" (also referred to as "establishing potential") describes how the person feels when he believes that he possesses the ability to pursue his aspiration; "experiences" (also referred to as "experiencing process") describes how the person feels when he is successfully progressing toward his aspiration; and "outcomes" (also referred to as "creating potential") describes how the person feels when he has achieved his aspiration.

The example motivational matrix 200 includes nine motives, each motive representing a combination of focus of aspiration and level of aspiration. The nine motives include security 202, empowerment 204, belonging 206, identity 208, engagement 210, nurturance 212, mastery 214, achievement 216, and esteem 218. For instance, the motive of "security" describes how a person feels when aspiring to establish potential within himself. The motive of "achievement" describes how a person feels when aspiring to create a product through his activities. Both positive and negative feelings are associated with each motive. For instance, the positive feelings "free" and "powerful" and the negative feelings "trapped" and "frustrated" are associated with the motive of empowerment. Further details about the motivational model and the motivational matrix 100 are provided in U.S. application Ser. Nos. 12/872,531 and 12/713,539 and in "Toward a unified model of human motivation" (Forbes, David L., *Review of General Psychology*, Vol. 15(2), June 2011, 85-98), the contents of all of which are incorporated here by reference in their entirety.

Each of the motives or aspirations described by the model represents one or more emotions experienced by the test subject 102 when the test subject 102 possesses the corresponding motive or aspiration and is exposed to a sensory stimulus that evokes that emotion or aspiration. For example, emotions such as feeling brilliant, superior, visionary, experienced, dominant, or excellent may be associated with the motive of mastery. Accordingly, when a test subject possesses the motive of mastery, he is likely to experience one of those emotions in response to certain sensory stimuli.

Example sensory stimuli and associated motives include images such as a person fastening a seat belt (security), a fingerprint (identity), a surgeon performing surgery (mastery), an airplane taking off (empowerment), several business professionals working together (engagement), an athlete wearing a medal (achievement), children playing together (belonging), a mother tending to a sick child (nurturance), and a military officer being decorated with ribbons (esteem). The sensory stimuli that are presented to the subject can be chosen because they are associated respectively with each of the nine motives in the chart. When the subject indicates a link between one of the sensory stimuli and the topic stimulus, it can be inferred that the motive with which that sensory stimulus is correlated.

Thus, the motivational matrix 200 may be used to interpret the underlying motives of the test subject 102 and to apply those interpretations in a business or non-business context. For example, a test subject who indicates a link between a sensory stimulus that is correlated with a motive of "engagement" in the context of a topic stimulus such as a commercial product may be expected to have a positive response (that might cause the person to buy the product) to a message having a participatory tone and a focus on engaging results. Messages, such as marketing messages, may be developed, based on the identified underlying motives of one or more test subjects, to appeal to individuals having similar underlying motives. For example, if subjects for whom the topic stimulus was a new model of WhizBang hybrid cars frequently linked an image in which neighbors were working together on a project to the new WhizBang model, one might infer that an advertising message that said "When the group wants to get a job done, the WhizBang can help" might stimulate those subjects to buy WhizBangs.

The test subject 102 is provided instructions 115 to respond to each sensory stimulus that evokes feelings that match (are associated with) the feelings elicited by the topic stimulus, e.g., as directed by the priming sentence. For example, if the topic stimulus is an advertisement for a brand of packaged food, the priming sentence is "Based on this commercial, I hope that eating this brand of food would make me feel _____," and the sensory stimulus is a picture of a family, then the test subject 102 is asked to respond if the picture of the family evokes an emotion that completes the priming sentence. The amount of time the test subject is given to respond to each sensory stimulus may be determined based on a test theory. For example, each sensory stimulus may be presented to the test subject long enough for simple recognition of the sensory stimulus to occur, but not so long that the test subject begins cognitive processing of the sensory stimulus. For instance, each sensory stimulus may be presented to the test subject for between about 500 and 1000 milliseconds, which we sometimes call the presentation period.

The test subject 102 responds to each sensory stimulus via an input device of the computing device 104, e.g., by pressing a key on a keyboard, clicking a mouse button, tapping a region of a touch screen, speaking, or interacting with another type of input device. In some examples, the test subject 102 may respond during the time in which the sensory stimulus is displayed (e.g., approximately 500-1000 milliseconds). In some examples, the test subject is also given a grace period for response e.g., of about 200-900 milliseconds, after the sensory stimulus is removed (i.e., after the presentation period) but before the next sensory stimulus is displayed. For instance, there may be a wipe period (e.g., of about 300 milliseconds) during which a first sensory stimulus is removed and a blank period (e.g., of about 500 milliseconds) between wiping of the first sensory stimulus and display of a second sensory stimulus. In one example, a response to a particular sensory stimulus is considered valid if it falls within a 1600 millisecond period starting at 100 milliseconds after onset of the sensory stimulus and ending at 500 milliseconds after the sensory stimulus is removed. In some examples, responses that occur early on in the display of a sensory stimulus (e.g., within about 100 milliseconds) are counted as responses to the previous sensory stimulus; in some examples, those early responses are disregarded as errors. Without wishing to be bound by theory, it is believed that showing a sensory stimulus for between 500 and 1,000 milliseconds is short enough that the response is only an emotional response with no cognitive aspect, i.e., the test subject does not have enough time to think about the response. The response may be a lack of response. In our specific example, given above, the subject would quickly respond to the picture of the family if the picture of the family triggered a non-cognitive emotional response from the subject.

The responses 101 to the sensory stimuli are stored in a temporary memory on the computing device 104 while the test is in progress. In some examples, the timing of the test subject's response to each sensory stimulus (e.g., the time difference between when the sensory stimulus was presented and when the test subject responded) is also measured and stored along with the responses. In some examples, when the survey is completed, a completed set of responses 125 is written to a survey database 120. In the example of FIG. 1, the survey database 120 is located on the server 110. In some examples, the survey database 120 is located on a different server or on the computing device 104. In some examples, a partial set of responses is written to the survey database 120 while the test is still in progress. For instance, during a test including 45 sensory stimuli, each group of five responses is written to the survey database as the test is ongoing, such that a total of nine groups of responses are written to the database. In some examples, an identifier for each test subject, such as a username or a numerical identifier, is stored in the survey database 120. For each test subject, identifiers of the sensory stimuli presented to the test subject are stored along with the test subject's response to each of the sensory stimuli. For instance, a positive response may be stored as a "1" and a lack of response or a response outside the response period may be stored as a "0." If the response time is measured, the response time for each stimulus image is also stored along with the identifier of the corresponding sensory stimulus. In some examples, the survey database 120 may also provide the ability to store textual notes, such as the moderator's notes about a follow-up conversation with the test subject.

In some examples, a linguistic expansion test is also presented to the test subject 102. For instance, emotional descriptor terms 123 are stored in a term database 121 and presented to the test subject in a further assessment battery to further define emotions that are revealed by the emotional survey. The test subject is prompted to respond to these terms, and the responses can be analyzed statistically to determine which of the terms are accurate descriptors of the test subject's emotional state. In one example, the terms are presented as a force choice exercise. In another example, the terms are presented in rapid sequence, and the test subject is instructed to choose words that describe an emotional state that is indicated by previously selected sensory stimuli. In this test, a range of terms describing nuances within a dominant emotional theme identified by the image exercise are presented (e.g., if "Mastery" is identified as a dominant emotional theme, the terms may include "Brilliant," "Accomplished," "Gifted," and "Exceptional"). Results of the linguistic expansion test further dimensionalize the emotional profiles that are revealed by the emotional survey and can be used, e.g., as a guide to developing details of tactical execution of business strategy.

Figure 3A:
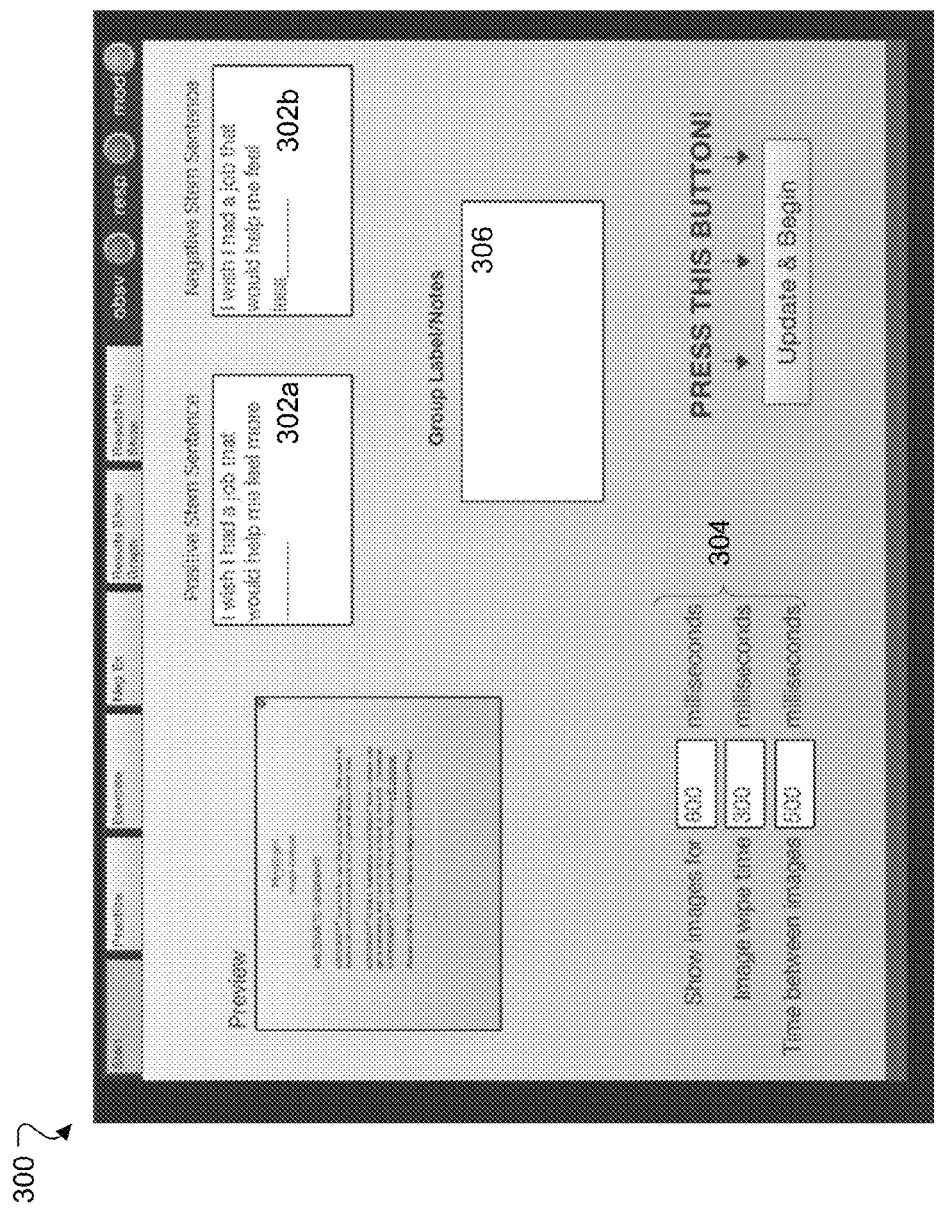
FIG. 3A-3E are screenshots of an example moderator interface.
Figure 3B:
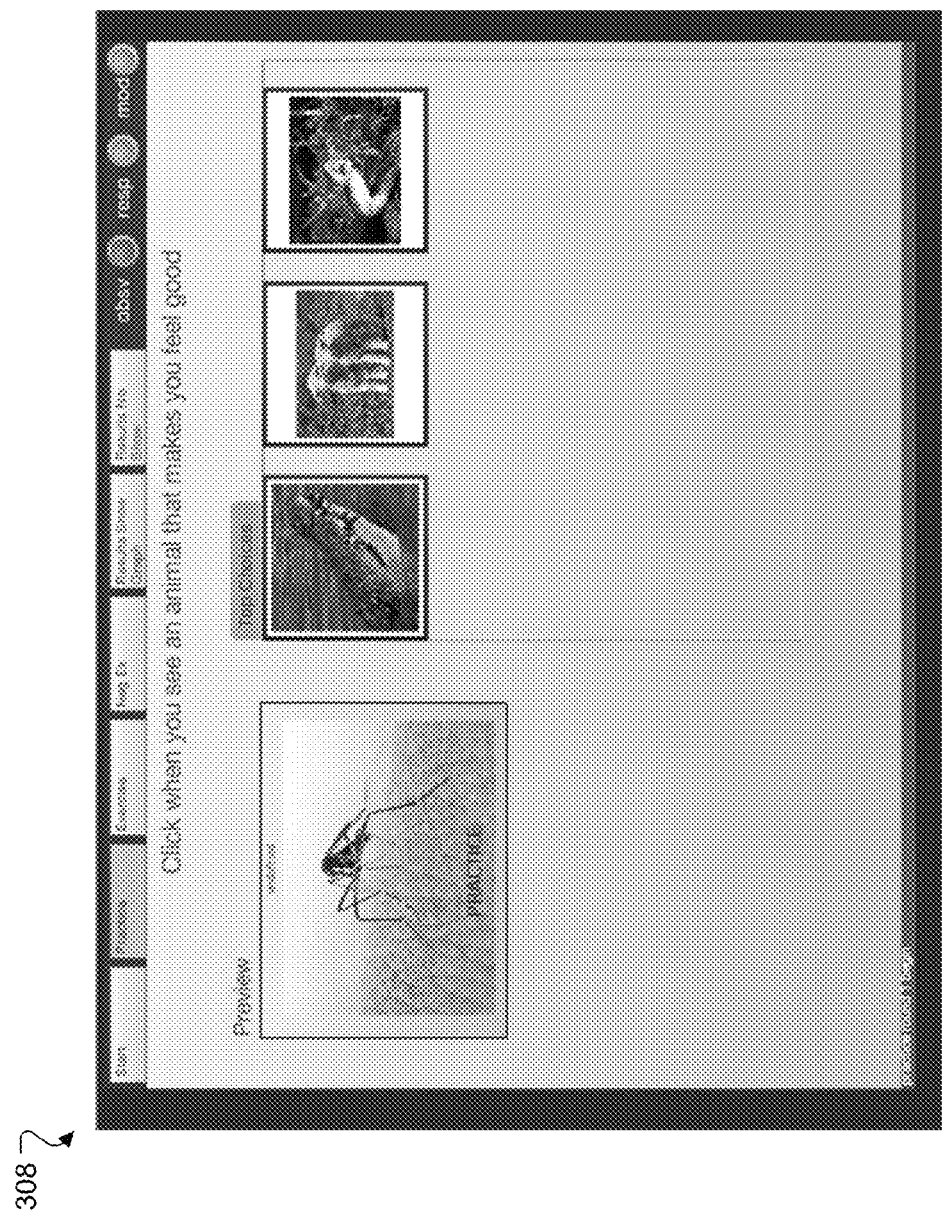
Figure 3C:
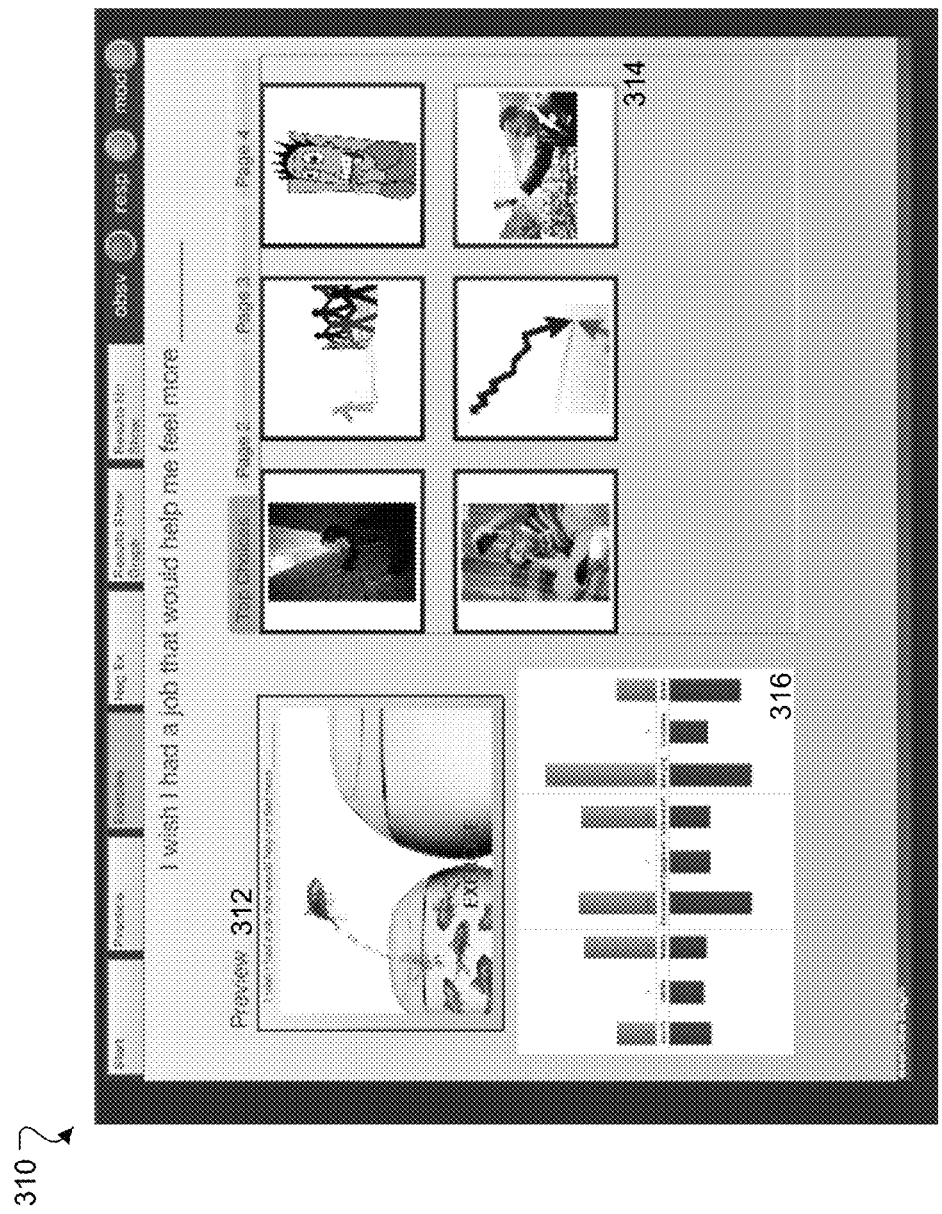
Figure 3D:
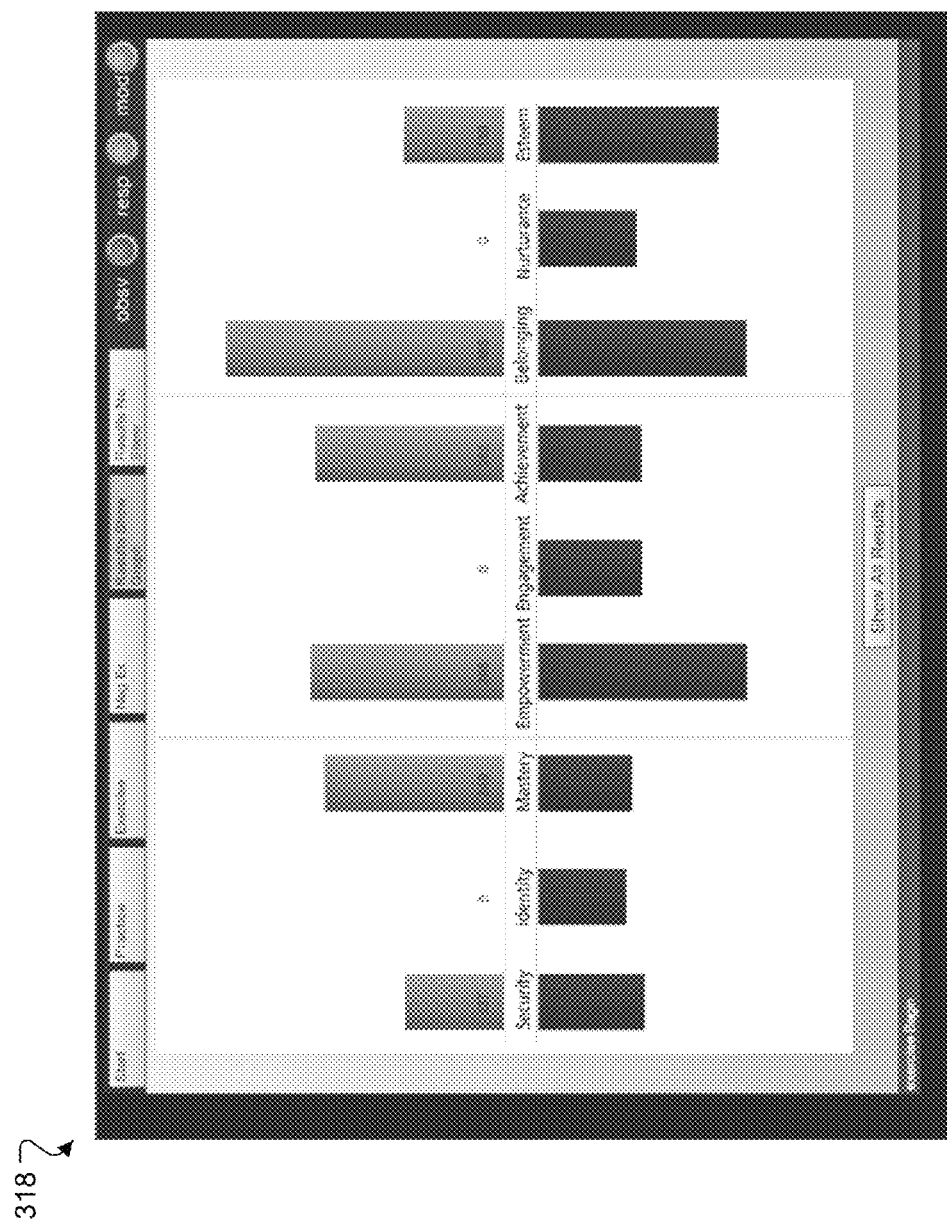
Figure 3E:
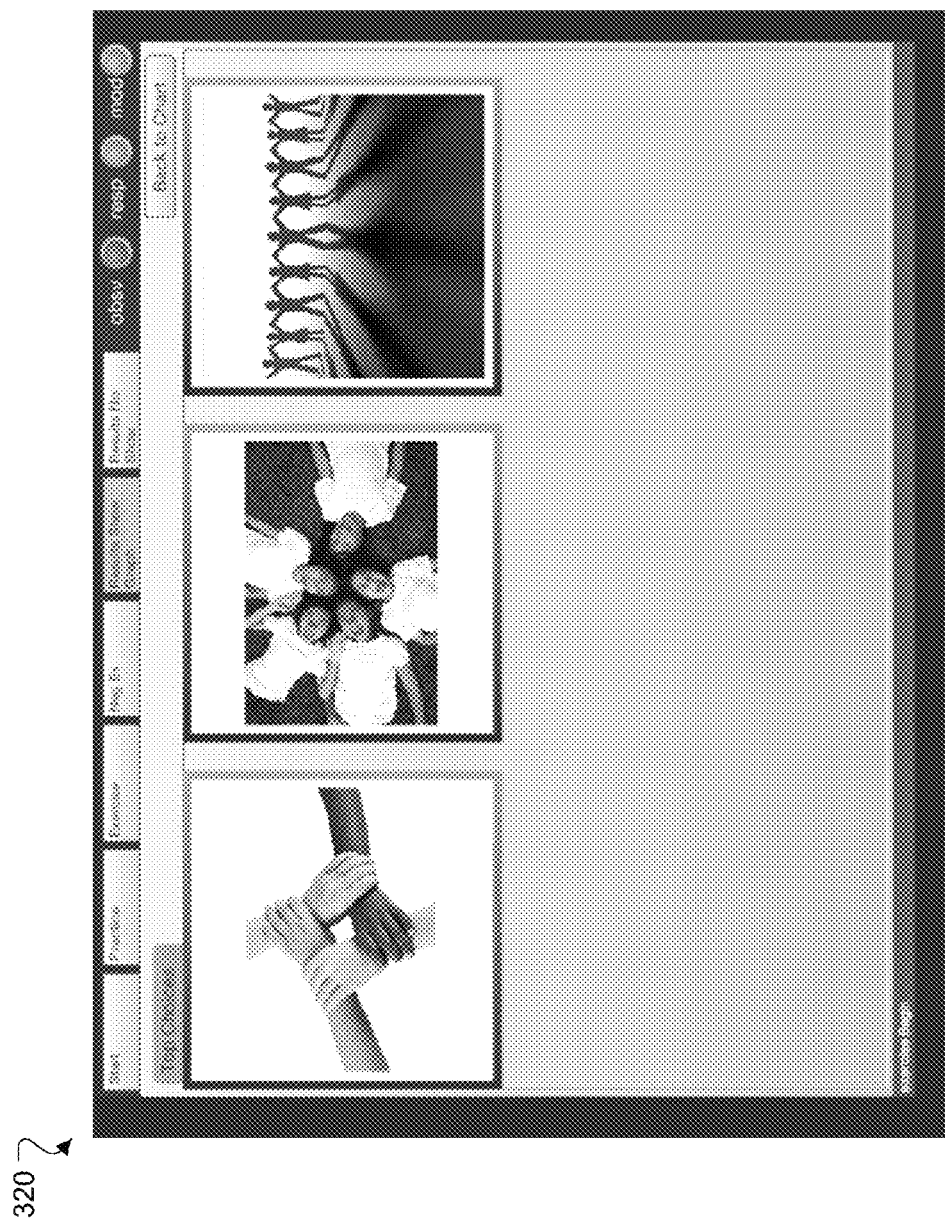

When the moderator 106 administers the survey, a moderator interface on the moderator's computing device 106 allows the moderator 106 to control the display of the survey on the test subject's computing device 104, as well as the display of the survey on the observer's computing device. Screenshots of an example moderator interface are shown in FIGS. 3A-3E. The moderator interface allows the moderator 106 to view the setup of the survey via a configuration window 300 (FIG. 3A). The configuration window 300 shows the positive and/or negative priming sentences 302a, 302b, respectively, to be used for the survey and the image display timing 304. In some examples, the moderator can edit the priming sentences 302a, 302b and the timing 304. The moderator can also enter labels or notes 306 to be associated with the survey. In some examples, other configuration options are also available via the configuration window, such as the ability to select whether to display positive types of images and/or negative types of images and in what order the images are to be displayed to the test subject.

A practice window 308 (FIG. 3B) of the moderator interface allows the moderator to introduce the survey to the test subject via instruction pages and previews of sample survey pages. As the survey progresses, an exercise window 310 (FIG. 3C) of the moderator interface displays a real-time preview 312 of each stimulus image presented to the test subject 102 and a grid 314 of thumbnails of the stimulus images that were positively responded to by the test subject. In some examples, the thumbnails are ordered by how quickly they were selected by the test subject. A real-time graph 316 of the survey results is also shown in the exercise window 310.

A graphical results window 318 (FIG. 3D) and an image-based results window 320 (FIG. 3E) of the moderator interface enable the moderator to review a graphical display of the results, e.g., with the test subject or with an observer. In some examples, the results window is available to display real-time results during the survey. In some examples, the results window displays completed results after an individual test subject completes the survey or after a group of test subjects all complete the survey. The observer interface possesses generally the same display capabilities as the moderator interface but does not enable the observer to control or interact with the survey.

In some examples, demographic information 119, such as age, gender, marital status, parental status, race, income, or other information is also collected from the test subject. The demographic information 119 may be stored in a subject database 129 that contains information about test subjects or may be stored in the survey database 120 in association with the test subject's responses. The demographic information may be collected from the test subject by the survey administration engine 108, e.g., at the start or end of the survey, or may be collected by the moderator 106 and input into the computing device 104 or another computing device, such as a computing device 107 operated by the moderator. In addition, information 127 about the test subject's consumption habits, such as the test subject's history of or preference for shopping at certain stores or purchasing certain brands, may also be collected from the test subject and stored in the survey database 120 in association with the test subject's responses. The consumption information may be collected from the test subject by the survey administration engine 108, e.g., at the start or end of the survey, or may be collected by the moderator 106 and input into the computing device 104 or another computing device, such as the computing device 107 operated by the moderator.

In some examples, one or more databases include tables that store configuration information, information about test subjects, and survey results. An Setup table (e.g., in configuration database 109 shown in FIG. 1) stores configuration information for a particular emotional survey, including, e.g., the following variables:

Msid—a unique id for the particular emotional survey.
Specs—the survey definition (xml format).
MemberID—reference to the owner of the survey (i.e., the moderator).
Title—title of the survey.
dateAdded—date/time stamp.
template (Yes/No)—whether this survey definition should be used as a template for future emotional surveys.
practice (Yes/No)—whether this survey definition uses a practice exercise.
studyType—reference to the type of survey. This variable may be used in a configuration interface to filter options for pre-defined priming sentences.

A Users table (e.g., in subject database 129 shown in FIG. 1) stores information about test subjects, including, e.g., the following variables:

Userid—a unique identifier generated by the system and used in the Results table (see below) to identify related records.
Username—optional field to hold a text-based user name.
Msid—reference to an emotional survey and associated configuration to which the test subject belongs.
Uservar1,uservar2,uservar3—demographic or other information specific to the test subject. This variable may be used, e.g., to filter or cut when analyzing the results of a survey.

An Results table (e.g., in survey database 120 shown in FIG. 1) stores results of the emotional surveys. The Results table contains a separate record for each image selected by a user. For each record, the following data is stored:

Userid—the unique identifier of the test subject (assigned in the Users table).
Msid—reference to the emotional survey to which the test subject belongs.
Imageid—an identifier of the image (e.g., assigned in an image data table in image database 114 shown in FIG. 1).
Etime—the elapsed time between the moment the image was presented and when the test subject selected the image.
Score—a calculated score for that image (normalized against the range of times of all images selected by the test subject).
dateAdded—date/time stamp.

An analysis engine 124 analyzes the responses from an individual test subject or multiple test subjects and generates a report 127. The report may be displayed on the computing device 104, the moderator's computing device 107, or a computing device 126 operated by an analyst 128. The analysis engine 124 may receive input from the moderator 106, the analyst 128, or another party specifying characteristics of the report, such as a display format. The input may also specify that the report is to be generated based only on responses from test subjects that fall into certain demographic categories, that are or are not users of a certain product or patrons of a certain store, or other segmentations of the test subjects. In some examples, the report is a simple listing of, e.g., the emotion associated with each sensory stimulus and the test subject's response to each sensory stimulus. In some examples, the report includes, e.g., a summary of the responses of many test subjects and/or charts or graphs of the responses. The report may also include a motivational profile of the test subject(s) and/or recommendations based on the results, as discussed in greater detail below. For instance, the recommendations may be of use to marketers, advertisers, or other business professionals in making decisions regarding marketing, such as advertising, branding, or product development. The report can be shared with a client or can be an input to a larger analysis/report.

In some examples, an analysis interface is displayed on one or more of the test subject's computing device 104, the moderator's computing device 107, the analyst's computing device 128, or another computing device. The analysis interface may be used for quantitative or qualitative analysis of the responses from an individual test subject or multiple test subjects. For instance, the analysis interface may allow an analyst or other operator to select motivational profiles for various subsets of a group of test subjects for further quantitative and/or qualitative analysis. The subsets of the group of test subjects may be grouped based on, e.g., demographic characteristics (e.g., one or more of age, gender, income range, educational level, or other demographic characteristics), consumption characteristics (e.g., consumers of a particular brand), characteristics of the results (e.g., all subjects for whom "Mastery" was the dominant element in the emotional profile), or a combination of one or more of these characteristics. The analysis interface may display graphical visualizations of emotional profiles (e.g., bar charts depicting the frequency of each of a variety of emotions), images chosen most often among a particular subgroup, words chosen most often to describe nuances of a particular emotional motive (e.g., words chosen to describe types of mastery), and other quantitative and qualitative results.

Figure 4:
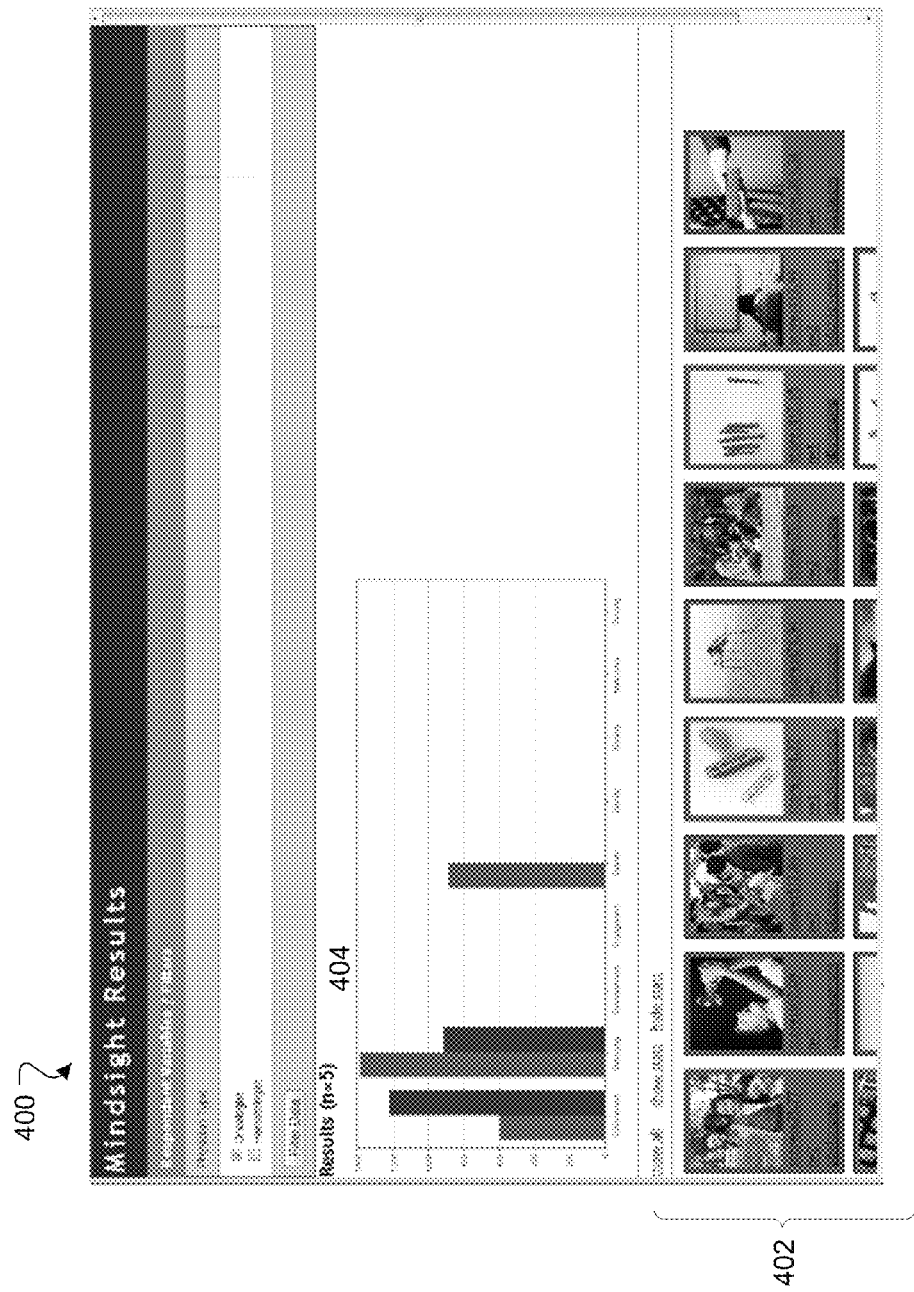
FIG. 4 is a screenshot of an example results report.

An example report 400 is shown in FIG. 4. The report 400 includes thumbnails of the stimulus images 402 selected by the test subject and a graph 404 depicting the distribution of results across the motivational domains.

In one example, the emotional survey was used to assist a major beverage company in testing two potential advertisements for a new product. Traditional advertising testing indicated that both advertisements were equally strong in generation of purchase interest, which is a traditional measure of advertising impact. The emotional survey was used to understand which of the two advertisements was most effective in generating a compelling emotional impact among consumers exposed to the advertisement. Test subjects were shown one or both of the potential advertisements and then administered the survey. The responses of the test subjects to each of a number of sensory stimuli were collected and analyzed to identify the most common emotions elicited by the advertisements. The survey clearly indicated that the two advertisements elicited different distinctive emotional impacts and that one of the two advertisements created a stronger emotional promise, namely that the product would generate an appealing drinking experience (the emotion of engagement) and improve family meal times (the emotion of belonging).

In some implementations, the survey is administered according to a configuration file 130, e.g., an Extensible Markup Language (XML) file, which includes links or pointers to the topic stimulus and sensory stimuli to be used for the survey, the stimulus display period, the period for the test subject to respond to the sensory stimulus, and other information relevant to survey administration. In some examples, multiple exercises can be defined in a single configuration file.

Figure 5A:
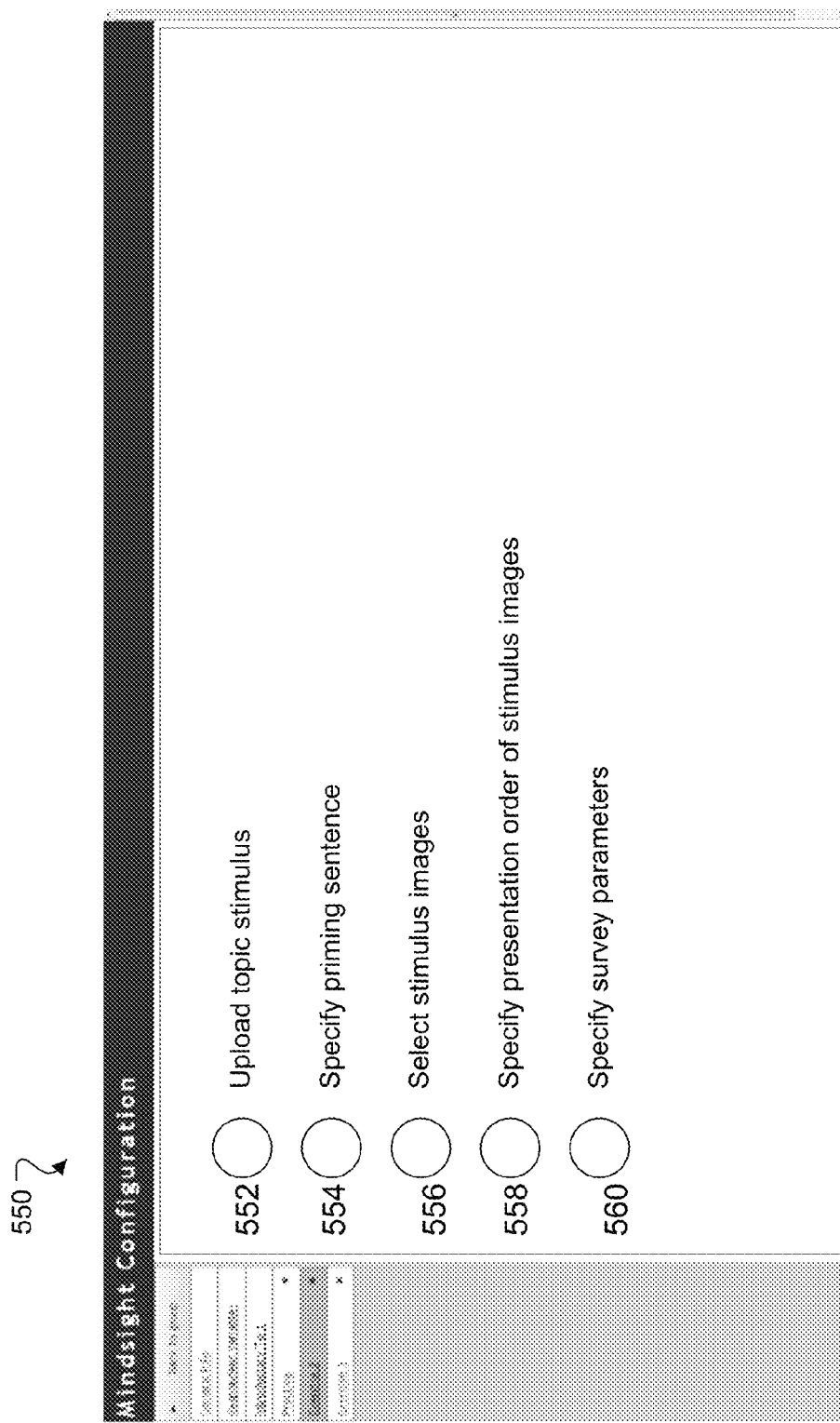
FIG. 5A is an example configuration interface.

The moderator 106, a system administrator 132, or another party can edit the configuration file via a self-service (e.g., web-based) configuration interface 133 to specify a desired configuration for a survey. An example configuration interface 550 is shown in FIG. 5A. For instance, the configuration interface 550 allows the system administrator to upload an advertisement, statement, or other item to be used as the topic stimulus (button 552); select or specify one or more priming sentences (button 554); select specific stimulus images to be presented (button 556); specify the presentation order of the stimulus images (button 558); and specify other parameters for the survey (button 560).

Figure 5B:
FIG. 5B is a screenshot of an example configuration interface.

A stimulus image selection screen of an example configuration interface 500 is shown in FIG. 5B, showing that five images 502 have been selected from a pool 504 of possible positive achievement images. The configuration interface also allows the operator to specify respondent characteristics of the subject(s) to whom the survey is administered, including, e.g., demographic information and/or information about the subjects' consumption habits. These characteristics may later be specified as sorting criteria via an analysis and reporting interface, such as when the results of the survey are viewed along with results from other surveys or other types of exercises in a research study (described in more detail below).

Figure 6:
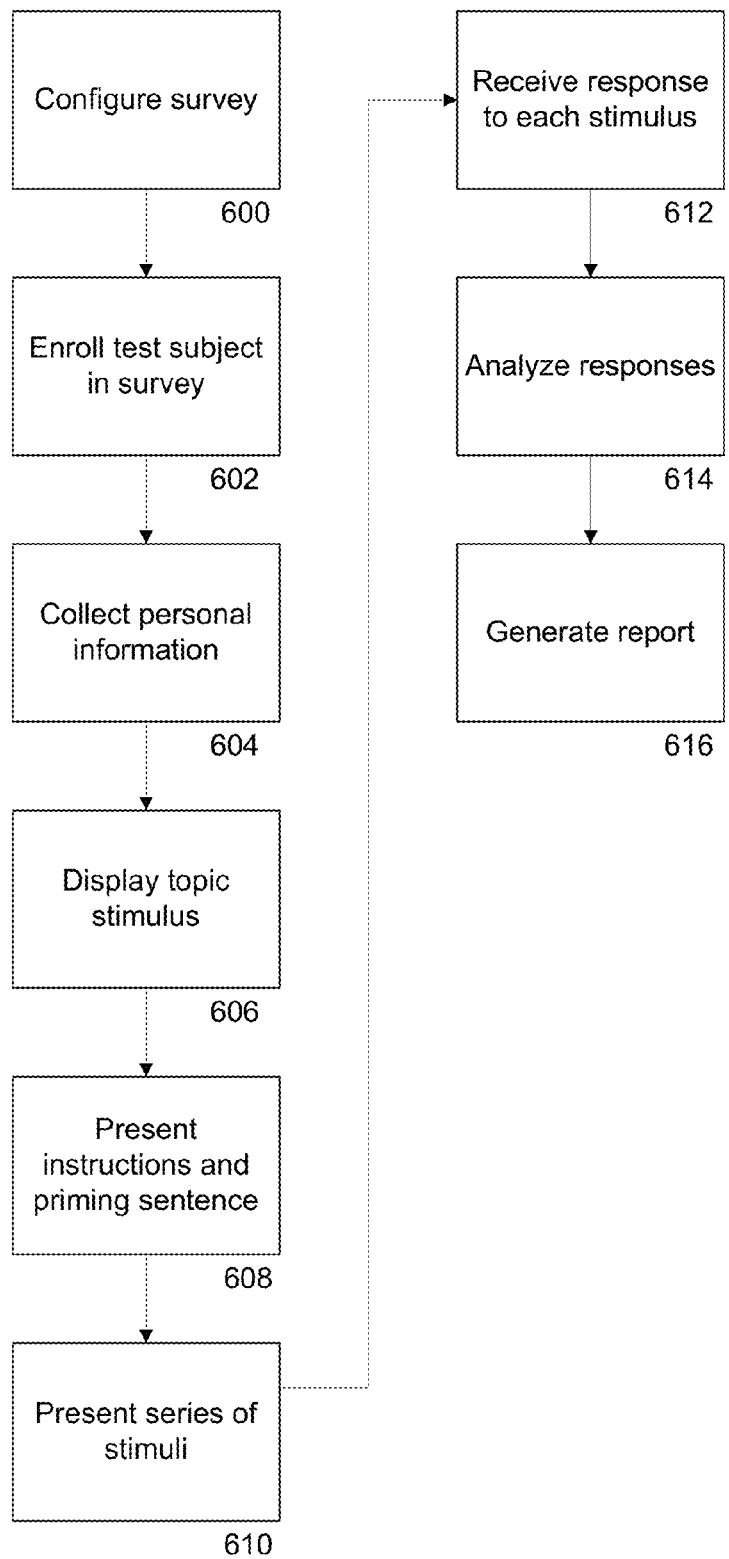
FIG. 6 is a flowchart of an example process for administering and analyzing the results of an emotional survey.

FIG. 6 shows an example of a process for administering and analyzing the results of an emotional survey. Further details regarding the administration of the emotional survey are provided in U.S. patent application Ser. Nos. 12/872,531 and 12/713,539, the contents of both of which are incorporated here by reference in their entirety. For the purposes of this example, the sensory stimuli are assumed to be still images, but other sensory stimuli may also be used.

The survey is configured (step 600) by an operator via the configuration interface, including specification and/or upload of the topic stimulus (e.g., an image of a product, an advertisement, or a brand slogan) and selection and/or specification of one or more priming sentences. The configuration interface allows the operator to specify values for one or more of the stimulus display period, a stimulus fade-away period (as the image is being wiped away), the rest interval (no image is displayed), and the grace period for response; default values are used if the operator does not specify the values.

For instance, the default stimulus display period may be between about 500 milliseconds (ms) and 1 second, the fade-away period for about 200-400 milliseconds (e.g., about 300 milliseconds), the rest interval for about 400-600 milliseconds (e.g., about 500 milliseconds). The configuration interface allows the operator to select stimulus images, if desired, or to indicate that the stimulus images are to be selected at random. The operator can also specify the presentation order of the stimulus images, either in terms of specific images or in terms of the emotions associated with the images. In addition, the operator can select whether stimulus images associated with positive emotions, negative emotions, or both, are presented, and the order in which the types of images are presented.

The test subject is enrolled in the survey (step 602). In some examples, the moderator initiates the survey for the test subject (e.g., in a focus group or interview setting); in some examples, the test subject initiates his own survey (e.g., in response to an email solicitation). In some examples, the emotional survey is part of a longer survey (e.g., a quantitative web survey), and the test subject has already enrolled in an earlier portion of the survey. By enroll, we mean that the test subject has agreed to participate in the survey, has consented to any relevant waivers, and may have logged into the survey system or created an account with the survey system.

Prior to beginning the survey, personal information is collected (step 604) about the test subject, including demographic information, e.g., age, gender, marital status, parental status, race, income, or other demographic information; and information about the test subject's consumption habits, e.g., the test subject's history of or preference for shopping at certain stores or purchasing certain brands. In some examples, identifying information about the test subject is also collected, including, e.g., name, email address, home address, and/or telephone number. For instance, such identifying information may be collected if a prize is offered to selected respondents who complete the survey. The personal information may also be collected at the end of the survey. Any personal information collected may be privacy protected. In some examples, non-personal information may be used openly, e.g., for statistical analysis of the data.

At the start of the survey, the topic stimulus (e.g., an image of a product, an advertisement, or a brand slogan) is displayed to the test subject (step 606). For instance, an advertisement for a brand of dish detergent may be presented. If the topic stimulus is a video, the test subject is prompted to start the video, e.g., by a mouse click or a tap on a touch screen. In some examples, the topic stimulus is presented for a limited amount of time (e.g., for a default amount of time or for an amount of time specified during configuration of the survey). In some examples, the topic stimulus is presented for an unlimited amount of time until the test subject indicates (e.g., by a mouse click or a tap on a touch screen) that he is ready to continue.

A priming sentence related to the topic stimulus is presented to the test subject (step 608). For instance, after presentation of the dish detergent advertisement as the topic stimulus, the priming sentence may state "Based on this advertisement, I would hope that purchasing this brand of dish detergent would make me feel a little more . . . " (i.e., a positive priming sentence) or "Based on this advertisement, I worry that purchasing this brand of dish detergent would leave me feeling a little bit . . . " (i.e., a negative priming sentence). The test subject is given instructions for how to respond to the stimulus images that will follow the priming sentence (step 608). For instance, the test subject may be instructed to respond to the stimulus images that evoke emotions that would complete the priming sentence. In some cases, the instructions and the priming sentence are presented together to the test subject. In some cases, the instructions and the priming sentence are presented separately; e.g., the instructions are presented before or after presentation of the priming sentence.

The stimulus images are presented to the test subject in rapid succession (step 610) according to the default time period or the time period specified during configuration of the survey. In some examples, at least nine stimulus images are presented, one stimulus image corresponding to each of the nine motives included in the motivational matrix of FIG. 2. In some examples, more or fewer than nine stimulus images are presented, e.g., 5-10 images per motive for a total of 45-90 total images. In some examples, a first set of stimulus images selected to evoke positive emotions is presented and a second set of stimulus images selected to evoke negative emotions is presented. In some examples, the images are presented in a random order; in some examples, the images are presented in sets of nine images, with each set of images including one image corresponding to each of the nine motives.

The test subject's response to each stimulus image is received and recorded (step 612). If the image evokes an emotion that the test subject associates with the topic stimulus, the test subject responds to the stimulus image, and the response is recorded as an affirmative response. If the image does not evoke an emotion that the test subject associates to the topic stimulus, the test subject does not respond to the stimulus image, and the lack of response is recorded.

In some examples, the responses are validated. For instance, if a response is received less than a lower bound threshold time (e.g., about 150 milliseconds) after the sensory stimulus is presented to the test subject, it is unlikely that the subject has had an adequate amount of time to recognize and react to the sensory stimulus in a meaningful manner. Such a response may be an erroneous response or an attempt by the test subject to subvert the test. Likewise, a response received more than an upper bound threshold time (e.g., about 300 milliseconds) after the presentation of the sensory stimulus ends is likely to occur after the test subject has had an opportunity to consciously process the response, and accordingly may be of marginal value in the assessment of the test subject's emotional characteristics. Responses having response times outside of the upper and lower bound threshold times may be characterized as invalid and may not be included in later analysis of the responses The responses are analyzed (step 614). For instance, for quantitative analysis, the responses to stimulus images corresponding to each of the nine motives are tallied, e.g., to determine a quantitative emotional profile of the test subject. The quantitative emotional profile represents the dominant emotional characteristics of the test subject and the relative strengths of these characteristics, as elicited by the topic stimulus. If the sensory stimuli to which the test subject responded affirmatively have been previously associated with a particular emotion, the response and response time may indicate the presence and/or strength of the emotion in the test subject. For instance, a shorter response time may indicate a higher strength of the emotion. The core motive of the test subject can be identified by classification of the emotions represented by the sensory stimuli that elicited positive responses from the test subject. For instance, if the majority of the sensory stimuli selected by the test subject are classified into the motive of security, then the presence of the security motive in the test subject may be inferred.

Because each sensory stimulus is known to elicit a particular emotional response, the dominant emotional characteristic of the test subject may be determined by analyzing the number of stimulus images with a positive response that share a particular emotional characteristic and the response time for each of those images. For example, if 45 stimulus images are presented, arranged in five cycles of nine images each, then each of the nine motives is represented by five different images. If the subject chooses more stimulus images representing one motive than any other, and/or if the subject chooses stimulus images representing one motive more quickly than images representing any other motive, then the test subject is likely to harbor that one motive as the dominant characteristic. Motives can be reported in a rank order beginning with the dominant, followed by the second most dominant, and so on.

In some examples, the responses are used as a quality score or weighting that determines the nature (e.g., salience, strength, or quality) of the emotional response from the test subject. The weighting may be based on the number of responses received that correspond to a particular element of the motivational matrix and/or according to the response time to each stimulus image. For instance, each positive response to a stimulus image is given a score based on how quickly the test subject responded to the stimulus image, such that responses having a shorter than average response time may be given more weight than those having a longer than average response time. The response time to a particular sensory stimulus may also be compared to response times to other sensory stimuli, or to the same sensory stimulus under different presentation conditions, to develop a score or weighting indicative of the quality of the response to that sensory stimulus. Responses having a greater weight are likely to indicate that the subject harbors the emotional characteristic associated with the respective sensory stimulus as the dominant characteristic. In some examples, the scores for each stimulus image are combined into scores for each of the nine motives (e.g., the motives of FIG. 1), for both positive and negative images, for a total of eighteen scores.

A report is generated (step 616) and presented to the moderator, an analyst, the test subject, or another party, or any combination of them. In some examples, such as in the context of an interview, the report is based on the scores for a single test subject. In some examples, such as in the context of a focus group or an online survey, the report is based on the scores for many test subjects. The report may be presented in text form (e.g., a listing of the motives ordered by score), in graphical form (e.g., a bar chart showing the positive and negative scores for each of the nine motives), or in another form. In some examples, the viewer of the report can switch between the text and graphical views. In some examples, each of the bars of the bar chart can be selected by the viewer, causing thumbnail views of the stimulus images corresponding to that motive to be displayed, e.g., ordered by the individual scores of the images. Each thumbnail can be enlarged, e.g., to full screen size. In some examples, a report may be generated for a group of test subjects or a subset of a group of test subjects. The report may be generated according to input from the moderator, the analyst, the test subject, or another party, e.g., via the analysis interface.

In some examples, the report includes a more extensive analysis of the results including, e.g., a motivational profile of the test subject(s) whose results are included in the report. For instance, the motivational profile may describe motivational characteristics of the test subject(s) as related to the brand or product of the topic stimulus. As an example, following a survey that uses a car advertisement as a topic stimulus, the motivational profile may reveal that the test subjects are motivated by safety. Analysts may use the motivational profiles to make decisions regarding the marketing (e.g. advertising, branding, or product development) of products. For instance, given that the test subjects in the above example are motivated by safety, advertising for the car may be refined to place more of a focus on the safety features of the car.

In some examples, the report itself includes a recommendation based on the analysis of the results, e.g., based on the relative scores of each motive or based on the motivational profile. For instance, in the car advertising example, the report may include a recommendation that the advertising for the car place a focus on the safety features of the car. The recommendation may also be a negative recommendation. For instance, if the responses indicate that the test subjects are not motivated by empowerment, then the report may include a recommendation that the advertising for the car not emphasize the power or speed capabilities of the car.

In some examples, the reports and analysis are based on a subset of the responses. For instance, trend reports may be generated based on responses filtered for gender, income level, or other demographic category, to enable analysis of trends in segments of the population. The reports may also be generated for test subjects who are or are not users of a product or brand or patrons of a store.

In some examples, large numbers of responses to large numbers of sensory stimuli are collected, for instance, from many test subjects. Statistical analysis of these responses may identify "clusters" of responses within the overall dataset, e.g., indicative of collective responses, such as predominant emotional states within the entire group of test subjects and/or within subgroups of test subjects.

The results may also be used to gain a qualitative understanding of emotional motives. For instance, in focus groups, in-person interviews, and telephone interviews, the results of the emotional survey can be reviewed after the survey has been completed, as a means to further the discussion and for probing the test subject's feelings about the images that were selected.

FIGS. 7A-7J are screenshots of an example of an emotional survey to assess the emotional reaction of test subjects to a video advertisement for a fictitious General's department store.

Figure 7A:
Figure 7B:
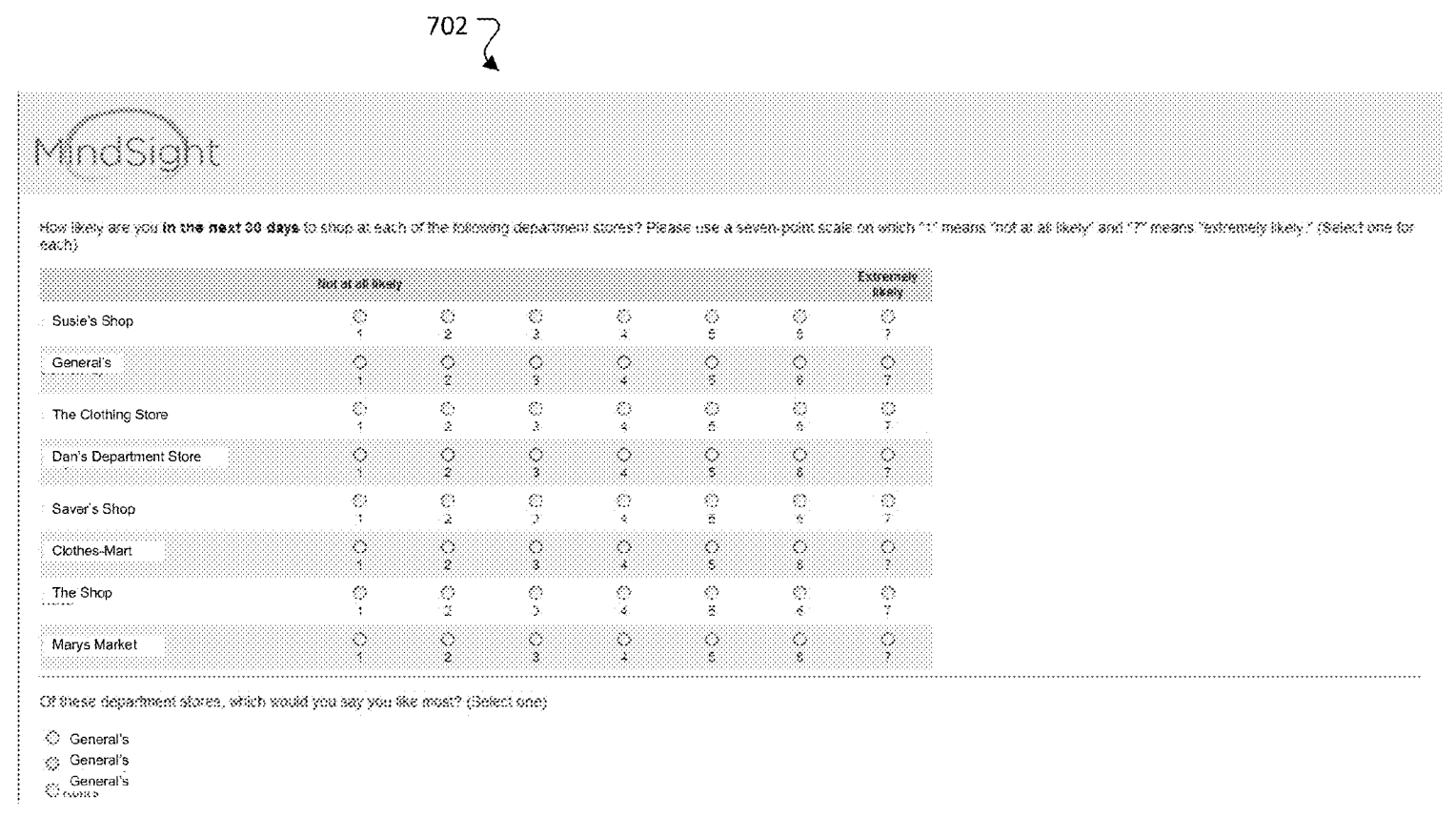

Referring to FIGS. 7A and 7B, prior to the emotional survey, a demographic questionnaire 700 is presented to gather information about the test subject's gender, age, and marital and parental status. A consumer history questionnaire 702 is also presented to gather information about the test subject's recent history of and preference for shopping at each of several department stores.

Figure 7C:
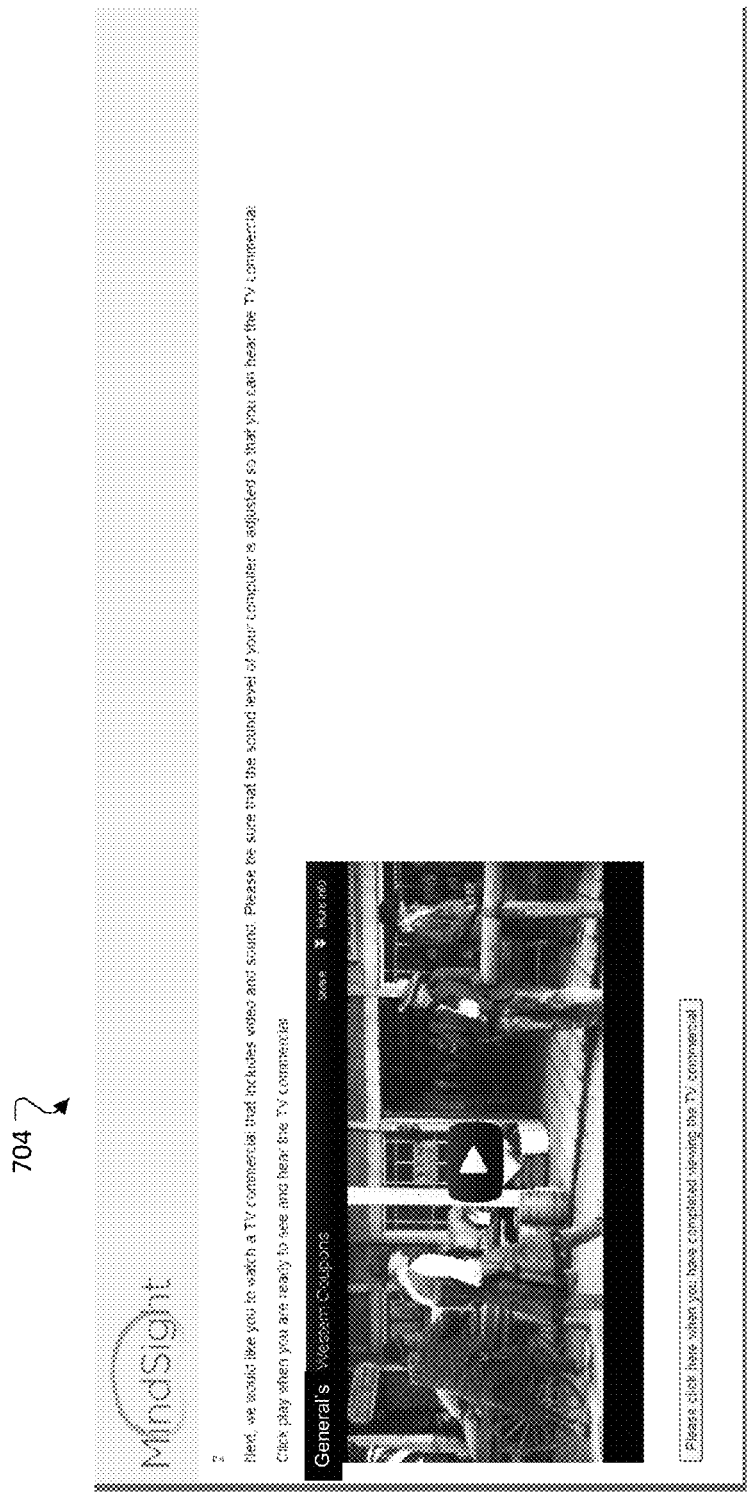

Referring to FIG. 7C, the topic stimulus for this example emotional survey is a video advertisement 704 for the fictitious department store General's. The test subject is asked to watch the video by clicking on the "Play" button.

Figure 7D:
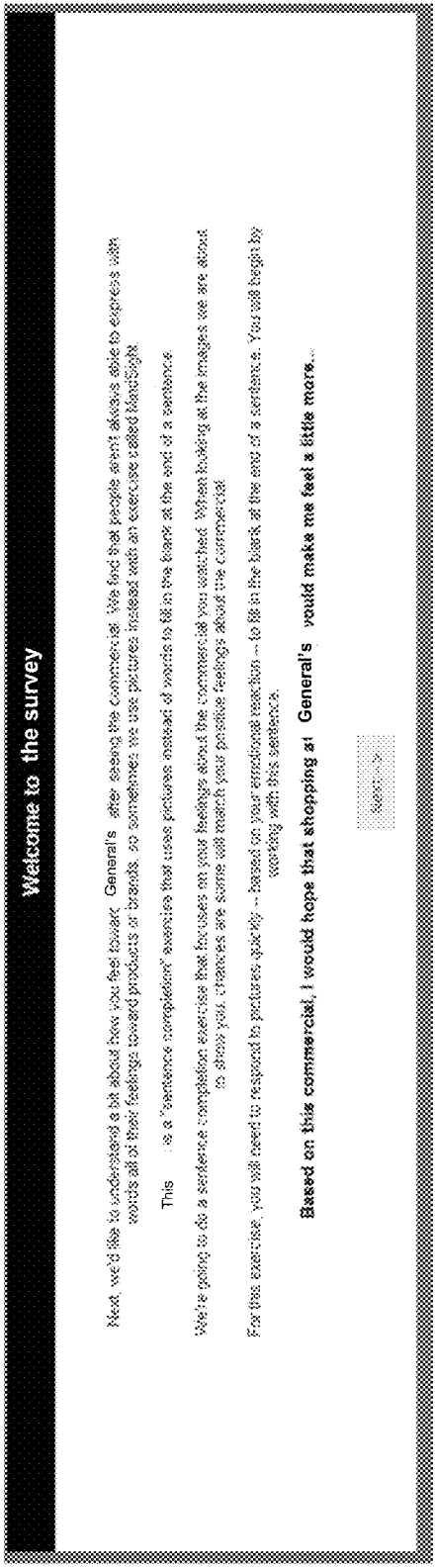

Referring to FIGS. 7D and 7E, once the test subject has watched the video advertisement, instruction screens 706 and 708 are presented instructing the test subject to indicate which of the following stimulus images evoke an emotion that completes the positive priming sentence "Based on this commercial, I would hope that shopping at General's would make me feel a little more . . . ."

Figure 7F:
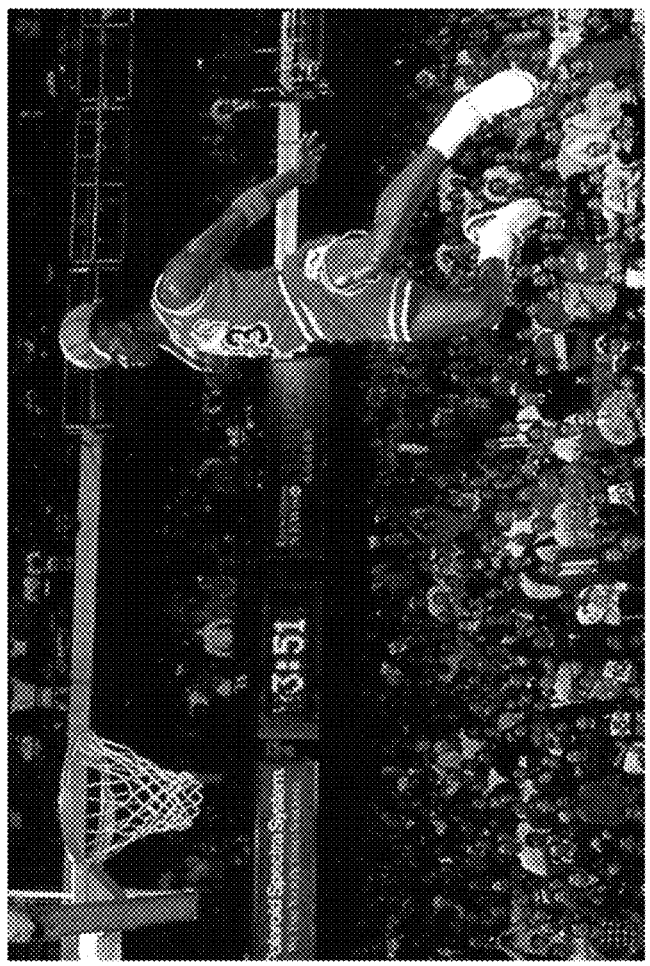
Figure 7G:

In the actual emotional survey, several (e.g., at least nine, or about 45-90) images are presented to the test subject as part of the positive sentence completion exercise. FIGS. 7F and 7G are two example stimulus images 710, 712. Image 710, of a basketball player about to dunk a basketball, may evoke positive emotions associated with the emotional motive of achievement. Image 712, of a mother hugging a child, may evoke positive emotions associated with the emotional motive of nurturance. For each stimulus image, the test subject is to respond (e.g., by clicking a mouse, pressing a key on a keyboard, or tapping a screen) if the emotion evoked by the image satisfies the sentence completion exercise.

Referring to FIG. 7H, after the images for the positive sentence completion exercise are shown, an instruction screen 714 is presented instructing the test subject to indicate which of the following stimulus images evoke an emotion that completes the negative priming sentence "Based on this commercial, I would worry that shopping at General's would leave me feeling a little bit . . . ."

Figure 7I:
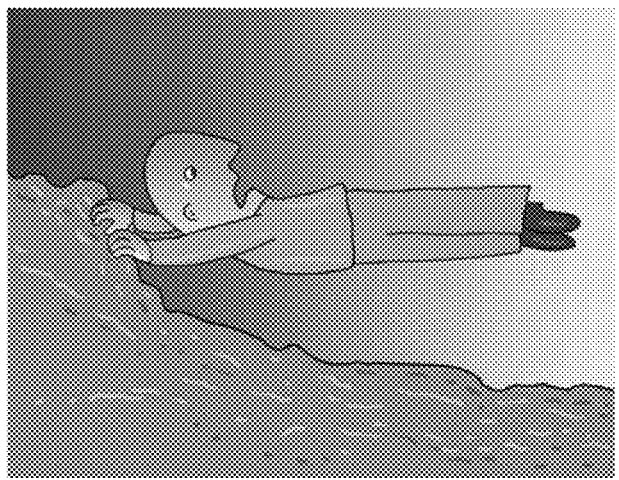
Figure 7J:
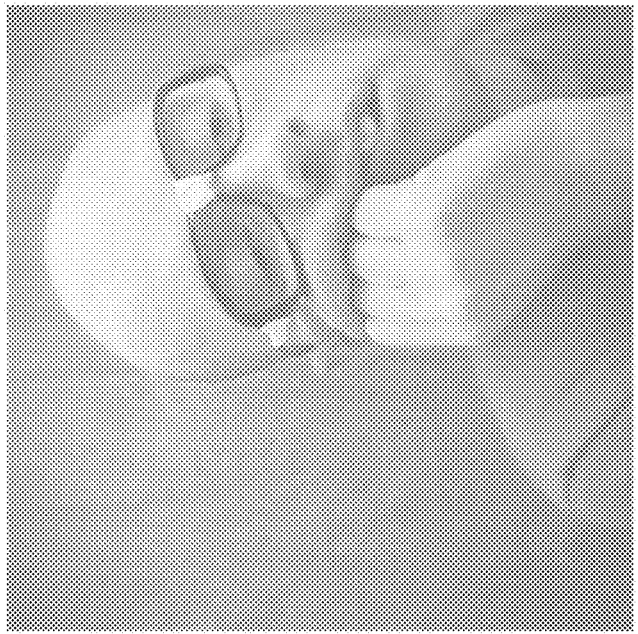

In the actual emotional survey, several (e.g., at least nine, or about 45-90) images are presented to the test subject as part of the negative sentence completion exercise. FIGS. 7I and 7J are two example stimulus images 716, 718. Image 716, a cartoon of a man hanging from a cliff, may evoke negative emotions associated with the emotional motive of security. Image 718, of a man who looks bored, may evoke negative emotions associated with the emotional motive of engagement.

Once the test subject's responses (i.e., positive responses and/or lack of response) are received and stored, the responses are analyzed. On a per-test subject level, the moderator may use the images to which the test subject did or did not respond to identify emotional motives that the test subject associates to the General's advertisement. For instance, if the test subject did not respond to the basketball image 710 but responded positively to the mother-child image 712, the moderator may determine that the General's advertisement evoked the feeling of nurturance but not of achievement. The responses for an individual test subject or for a small number of test subjects (e.g., in a focus group setting) may be used by the moderator to facilitate further discussion about the specific advertisement or the General's brand in general.

On a larger scale, the responses of many test subjects are aggregated and analyzed to determine typical emotional responses to the advertisement. The results may be used to drive marketing (e.g., advertising, branding, or product development) decisions.

Figure 8:
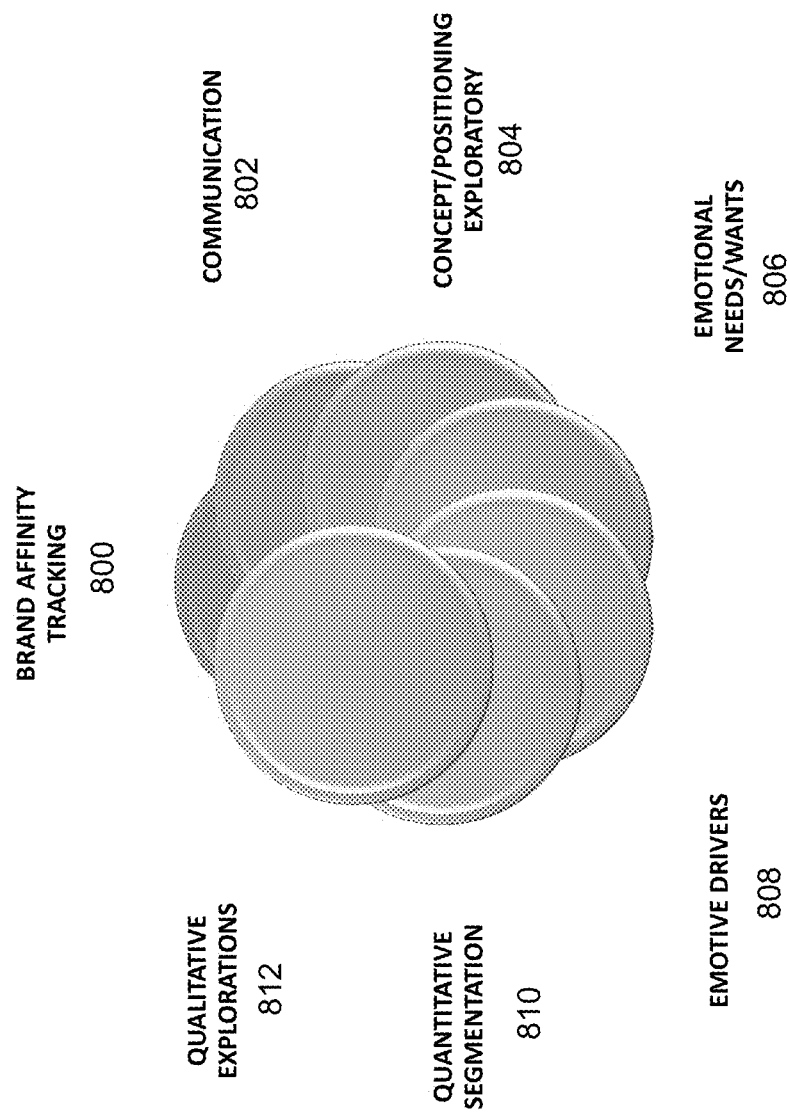
FIG. 8 is a diagram of example uses for the results of an emotional survey.

Referring to FIG. 8, the reports and recommendations, as well as other analysis of the survey results, can be used by marketers, advertisers, or other business professionals to make decisions regarding marketing (e.g., advertising, branding, or product development). For instance, the results may be used for brand affinity tracking (800), e.g., by revealing emotional connections that consumers have to an existing brand or seem disposed to develop to a potential new brand. The results may also be used to inform communication (802), e.g., for use in the development and/or testing of brand positioning and/or brand messaging. For instance, the results may be useful in exploring the alignment of messaging ideas with consumers' wants and needs in various product or brand categories.

The results may be useful in the exploration of product concepts or product positioning (804), e.g., to determine how a potential new product concept or new marketing approach for an old product resonates emotionally with consumers or to evaluate the emotional impact of a stimulus.

The results may reveal consumers' emotional needs and wants (806), in terms of both the consumers' lifestyles and the consumers' in-the-moment needs and wants. The results may also reveal consumers' emotive drivers (808), e.g., by identifying categories of brands or products that are associated with driving emotional motives, by identifying one or more of the nine motives as drivers for consumer behavior or by revealing consumers' emotional experiences while shopping.

The analysis may be useful in qualitative explorations of consumer emotions (810), e.g., by identifying key emotional motives in a product category. For instance, the results may be valuable in generating new emotional insights into consumer packaged goods (CPG) categories with leading brands with a long history.

Quantitative analysis applied to the results may also yield insights into consumer emotions and behavior (812). Quantitative communication testing (e.g., positioning and message testing) helps to identify the strength of the emotional impact of a communication stimulus and to profile the specific nature of the emotions aroused by the stimulus. Packaging may also be viewed as a communication device, and communication testing may also be used to identify impactful packaging and to profile the nature of the impact. Quantitative product concept testing helps to assess the emotional strength of product concepts, which can add emotional depth to traditional rational measures of purchase interest. Quantitative testing can also be used to determine and/or evaluate segmentation of a consumer population, e.g., by determining emotional motives that define a target segment or identifying consumers who fall into a target segment.

Figure 9:
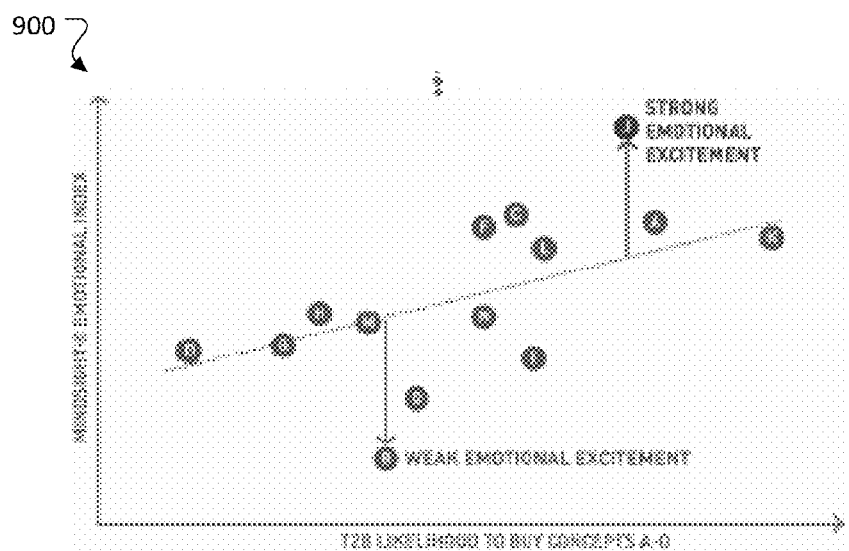
FIG. 9 is a plot of the results of an example application of an emotional survey.

Referring to FIG. 9, in one example application of the emotional survey described here, a packaged goods company wants to identify the "next big thing" in the product pipeline. Surveys were administered using product descriptions of one of fourteen potential new products as the topic stimulus, and emotional responses to the potential new products were collected and analyzed. For each product, an emotional index indicative of the emotional connection the test users exhibited toward the product was determined based on the responses. In addition, the likelihood that a consumer will purchase each potential new product was determined by traditional market research techniques. The emotional index versus the purchase likelihood was plotted for each potential new product to generate a plot 900 indicative of the relative potential for success of each product. In general, products in the lower left have a low likelihood of success (i.e., consumers have little emotional excitement about the products), while products in the upper right have a high likelihood of success (i.e., consumers have strong emotional excitement about the products). This example demonstrates the ability of the emotional survey to detect emotional connections that customers may feel to products.

In another example application of the emotional survey described here, a pharmaceutical company had been using a brand communication marketing approach for a drug in which a patient stated "I feel like I'm making the smart choice when using this drug." Sales of the drug were lackluster. After emotional surveys to explore emotions associated with the drug, it was determined that the dominant emotion associated with the drug was mastery, which suggested a marketing campaign based on the statement "I feel like I'm providing the best care of my patients when using this drug." After the marketing campaign began using the new approach recommended by the emotional survey, a 6% increase in prescriptions for the drug was observed.

Figure 10:
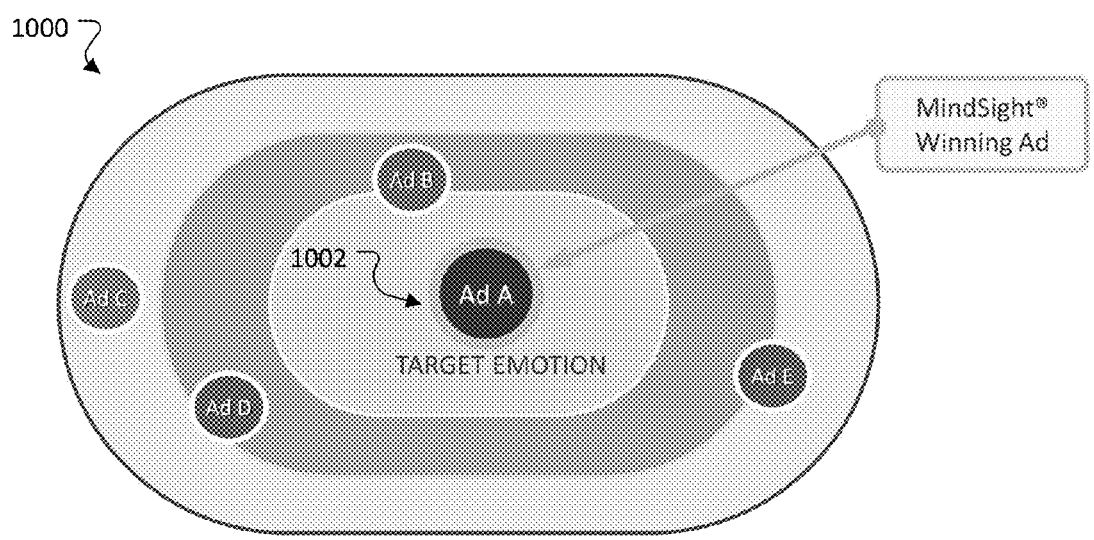
FIG. 10 is a diagram of the results of another example application of an emotional survey.

Referring to FIG. 10, in another example application of the emotional survey described here, a home care products company sought to develop advertisements to enhance its corporate image. A target emotion (engagement) was identified as the emotion that the company wanted to have associated with its corporate image. A number of potential advertisements were evaluated using emotional surveys to determine how well each potential advertisement aligned with the target emotion. The scores associated with the target emotion for each advertisement were displayed in a graphical representation 1000, providing a clear depiction of how well each advertisement succeeded in evoking the target emotion. One of the advertisements 1002 that best evoked the target emotion was selected. In later consumer surveys, it was found that consumers had improved recall and positive associations for the company and its brands, results that were indicative of a successful advertising campaign.

When the emotional survey is administered on a mobile computing device in real-world environments and in real time, the survey results can provide insights into real-time, in the moment emotions of the test subjects. For instance, prompting a consumer to access the survey in a store or even at a particular shelf of the store (e.g., by providing a scannable QR code on an in-store advertisement) can provide shopper insights into the effectiveness of packaging and point-of-purchase (POP) communications and into the overall shopping experience at the store. As another example, mobile device-based surveys can be used for emotional research at moments that happen naturally in the course of ordinary life, including occasions such as mealtimes, moments such as purchasing a snack from a vending machine, and episodes such as the onset of a health-related event (e.g., a headache or an allergy attack).

In some examples, the surveys described herein are presented in forms such as tests, games, or other types of assessments. For instance, in some examples, particularly for surveys administered on mobile computing devices, the surveys may be presented as games rather than as formal assessments.

The surveys described here are not limited to use with consumers or potential consumers. The surveys may also be used to probe emotional responses from other populations, including, e.g., employees, members of an interest group or a political party, or other groups of people. In addition, the surveys described here are not limited to evaluations of brands, but may also be used to evaluate other items or concepts.

The survey techniques described here are also relevant to human resources and organizational development applications. For instance, emotional surveys may be used to profile employee satisfaction or dissatisfaction, aid in workstyle coaching, assist in critical hiring cases, and other applications.

The survey techniques described here may also be used as a resource in the social affinity space, e.g., for matchmaking sites such as websites and mobile applications. For instance, emotional surveys may be presented as a game-like exercise to profile personal style preferences of members of the matchmaking sites.

Figure 11:
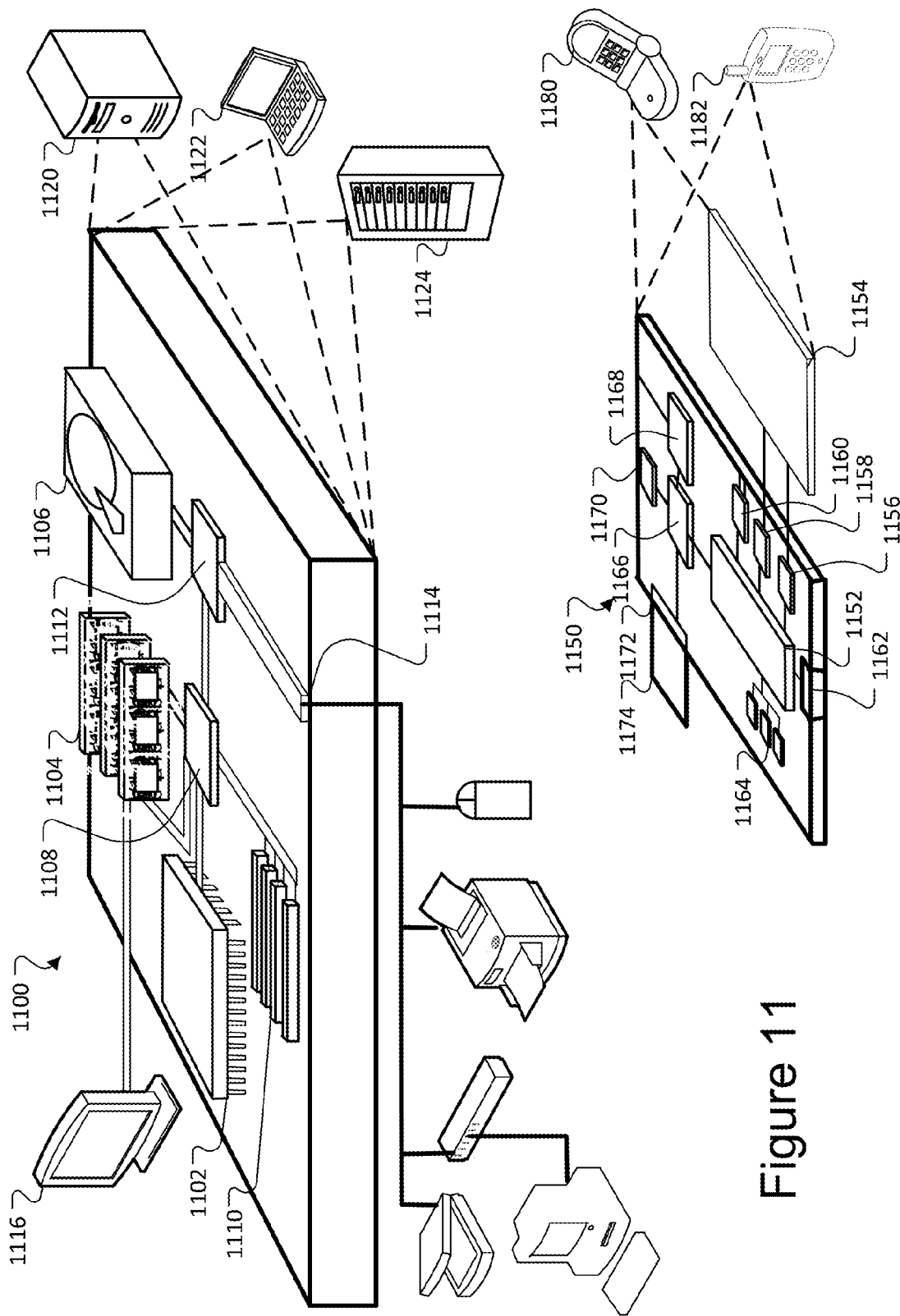
FIG. 11 is a block diagram of an example computer system.

FIG. 11 shows an example of a personal computing device 1100 and a mobile device 1150, which may be used with the techniques described here. For example, referring to FIG. 1, the computing devices 104, 122, 124 could be examples of the personal computing device 1100 or the mobile device 1150, and the media repository 108 could include one or more computer devices 1100. Computing device 1100 is intended to represent various forms of digital computers, such as laptops, desktops, workstations, personal digital assistants, servers, blade servers, mainframes, and other appropriate computers. Computing device 1150 is intended to represent various forms of mobile devices, such as personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 1100 includes a processor 1102, memory 1104, a storage device 1106, a high-speed interface 1108 connecting to memory 1104 and high-speed expansion ports 1110, and a low speed interface 1112 connecting to low speed bus 1114 and storage device 1106. Each of the components 1102, 1104, 1106, 1108, 1110, and 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as display 1116 coupled to high speed interface 1108. In other implementations, multiple processors and/or multiple buses may be used, as appropriate, along with multiple memories and types of memory. Also, multiple computing devices 1100 may be connected, with each device providing portions of the necessary operations (e.g., as a server bank, a group of blade servers, or a multi-processor system).

The memory 1104 stores information within the computing device 1100. In one implementation, the memory 1104 is a volatile memory unit or units. In another implementation, the memory 1104 is a non-volatile memory unit or units. The memory 1104 may also be another form of computer-readable medium, such as a magnetic or optical disk.

The storage device 1106 is capable of providing mass storage for the computing device 1100. In one implementation, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1104, the storage device 1106, memory on processor 1102, or a propagated signal.

The high speed controller 1108 manages bandwidth-intensive operations for the computing device 1100, while the low speed controller 1112 manages lower bandwidth-intensive operations. Such allocation of functions is an example only. In one implementation, the high-speed controller 1108 is coupled to memory 1104, display 1116 (e.g., through a graphics processor or accelerator), and to high-speed expansion ports 1110, which may accept various expansion cards (not shown). In the implementation, low-speed controller 1112 is coupled to storage device 1106 and low-speed expansion port 1114. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. It may also be implemented as part of a rack server system 1124. In addition, it may be implemented in a personal computer such as a laptop computer 1122. Alternatively, components from computing device 1100 may be combined with other components in a mobile device (not shown), such as device 1150. Each of such devices may contain one or more of computing device 1100, 1150, and an entire system may be made up of multiple computing devices 1100, 1150 communicating with each other.

Computing device 1150 includes a processor 1152, memory 1164, an input/output device such as a display 1154, a communication interface 1166, and a transceiver 1168, among other components. The device 1150 may also be provided with a storage device, such as a microdrive or other device, to provide additional storage. Each of the components 1150, 1152, 1164, 1154, 1166, and 1168, are interconnected using various buses, and several of the components may be mounted on a common motherboard or in other manners as appropriate.

The processor 1152 can execute instructions within the computing device 1150, including instructions stored in the memory 1164. The processor may be implemented as a chipset of chips that include separate and multiple analog and digital processors. The processor may provide, for example, for coordination of the other components of the device 1150, such as control of user interfaces, applications run by device 1150, and wireless communication by device 1150.

Processor 1152 may communicate with a user through control interface 1158 and display interface 1156 coupled to a display 1154. The display 1154 may be, for example, a TFT LCD (Thin-Film-Transistor Liquid Crystal Display) or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may be provide in communication with processor 1152, so as to enable near area communication of device 1150 with other devices. External interface 1162 may provide, for example, for wired communication in some implementations, or for wireless communication in other implementations, and multiple interfaces may also be used.

The memory 1164 stores information within the computing device 1150. The memory 1164 can be implemented as one or more of a computer-readable medium or media, a volatile memory unit or units, or a non-volatile memory unit or units. Expansion memory 1174 may also be provided and connected to device 1150 through expansion interface 1172, which may include, for example, a SIMM (Single In Line Memory Module) card interface. Such expansion memory 1174 may provide extra storage space for device 1150, or may also store applications or other information for device 1150. Specifically, expansion memory 1174 may include instructions to carry out or supplement the processes described above, and may include secure information also. Thus, for example, expansion memory 1174 may be provide as a security module for device 1150, and may be programmed with instructions that permit secure use of device 1150. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1164, expansion memory 1174, memory on processor 1152, or a propagated signal that may be received, for example, over transceiver 1168 or external interface 1162.

Device 1150 may communicate wirelessly through communication interface 1166, which may include digital signal processing circuitry where necessary. Communication interface 1166 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1168. In addition, short-range communication may occur, such as using a Bluetooth, WiFi, or other such transceiver (not shown). In addition, GPS (Global Positioning System) receiver module 1170 may provide additional navigation- and location-related wireless data to device 1150, which may be used as appropriate by applications running on device 1150.

Device 1150 may also communicate audibly using audio codec 1160, which may receive spoken information from a user and convert it to usable digital information. Audio codec 1160 may likewise generate audible sound for a user, such as through a speaker, e.g., in a handset of device 1150. Such sound may include sound from voice telephone calls, may include recorded sound (e.g., voice messages, music files, and so forth) and may also include sound generated by applications operating on device 1150.

The computing device 1150 may be implemented in a number of different forms, as shown in the figure. For example, it may be implemented as a cellular telephone 1180. It may also be implemented as part of a smartphone 1182, personal digital assistant, tablet computer, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used here, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well. For example, feedback provided to the user can be any form of sensory feedback (e.g., visual feedback, auditory feedback, or tactile feedback). Input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other implementations are also within the scope of the following claims.

The invention claimed is:

1. A method comprising:
    presenting, on a user interface of a computing device, a media item to a test subject, the media item associated with a brand or product;
    presenting, on a user interface of a computing device, sensory stimuli to the test subject, the presenting including, for each sensory stimulus:
        presenting the sensory stimulus for a first limited period of time, the duration of the first limited period being enforced by computer to have a predefined duration of more than about 500 milliseconds and less than about 1000 milliseconds, the duration of the first limited period of time being insufficient to enable conscious cognitive reflection on the sensory stimulus by the test subject,
        ending the presenting of the sensory stimulus at the end of the first limited period of time,
        providing a grace period immediately following the end of the first limited period of time, the duration of the grace period being enforced by computer to have a predefined duration of up to 300 milliseconds during which the sensory stimulus is not presented, and
        presenting a subsequent sensory stimulus at the end of the grace period;
    receiving from the test subject a response to the presentation of at least one sensory stimulus, including receiving the response within a second limited period of time that includes the first limited period of time and the grace period, the duration of the second limited period of time being insufficient to enable conscious cognitive reflection on the stimulus by the subject,
    the response to the presentation of a particular sensory stimulus indicative of a precognitive emotional reaction of the test subject to the particular sensory stimulus; and
    based on the received responses of the test subject to the sensory stimuli, generating, using an analysis module of a computing device, results suitable to inform a decision related to marketing of the brand or product.

2. The method of claim 1, wherein generating results includes generating a textual or graphical summary of the responses of the test subject to each of multiple sensory stimuli.

3. The method of claim 1, wherein generating results includes identifying an emotion associated with the media item.

4. The method of claim 1, wherein generating results includes generating a motivational profile of the test subject.

5. The method of claim 1, wherein generating results includes generating a recommendation related to marketing of the brand or product.

6. The method of claim 5, wherein generating a recommendation includes:
    identifying an emotion associated with the media item; and
    generating a recommendation for a marketing campaign based on the identified emotion.

7. The method of claim 1, wherein presenting the media item includes presenting the media item to a plurality of test subjects;
    presenting the sensory stimulus includes presenting the sensory stimulus to each of the plurality of test subjects; and
    wherein generating results includes generating results based on responses of each of the plurality of test subjects to the sensory stimulus.

8. The method of claim 7, wherein generating results includes generating results based on a subset of responses of the plurality of test subjects to the sensory stimulus.

9. The method of claim 8, wherein generating results includes filtering the responses to obtain the subset of responses.

10. The method of claim 1, wherein presenting a media item includes presenting at least one of a text-based item, an image, and a video.

11. The method of claim 1, wherein presenting a media item includes presenting an expression of a subject or an idea.

12. The method of claim 1, wherein presenting a media item includes presenting at least one of an image of a product, an image associated with a brand, an advertisement, a video of a product, a video associated with a brand, a brand slogan, and a product slogan.

13. The method of claim 1, comprising presenting a priming sentence.

14. The method of claim 1, wherein presenting the sensory stimulus includes presenting an image.

15. The method of claim 1, wherein the response of the test subject to the sensory stimulus is indicative of an emotion the test subject feels toward the sensory stimulus and the media item.

16. The method of claim 7, wherein generating results includes identifying a trend based on at least some of the responses of the plurality of test subjects.

17. The method of claim 7, wherein generating results includes identifying a cluster of similar responses from the responses of the plurality of test subjects.

18. The method of claim 7, wherein identifying a cluster of similar responses includes identifying responses to sensory stimuli that are associated with similar emotions.

19. A method comprising:
    for each of multiple test subjects:
        presenting a media item to the test subject, the media item associated with a brand, a product, or a situation;
        presenting sensory stimuli to the test subject, the presenting including, for each sensory stimulus:
            presenting the sensory stimulus for a first limited period of time, the duration of the first limited period being enforced by computer to have a predefined duration of more than about 500 milliseconds and less than about 1000 milliseconds, the duration of the first limited period of time being insufficient to enable conscious cognitive reflection on the sensory stimulus by the test subject,
            ending the presenting of the sensory stimulus at the end of the first limited period of time, providing a grace period immediately following the end of the first limited period of time, the duration of the grace period being enforced by computer to have a predefined duration of up to 300 milliseconds during which the sensory stimulus is not presented, and presenting a subsequent sensory stimulus at the end of the grace period;

receiving from the test subject a response to the presentation of at least one sensory stimulus, including receiving the response within a second limited period of time that includes the first limited period of time and the grace period, the duration of the second limited period of time being insufficient to enable conscious cognitive reflection on the stimulus by the subject; and based on the received responses from each of the test subjects, determining an emotional state of at least some of the test subjects with respect to the brand, product, or situation.

20. The method of claim 19, comprising determining the emotional state of at least some of the test subjects based on a cluster of similar responses received from at least some of the subjects.

21. The method of claim 20, comprising identifying the cluster of similar responses based on identifying responses to sensory stimuli that are associated with similar emotions.

22. The method of claim 20, comprising identifying the cluster of similar responses based on a statistical analysis of the responses received from at least some of the test subjects.

23. The method of claim 19, comprising identifying a theme associated with the emotional state of at least some of the test subjects.

24. The method of claim 23, comprising identifying the theme based on similar responses received from each subject of a subset of the test subjects.

25. The method of claim 19, comprising identifying a subset of the test subjects having a common demographic characteristic, and wherein determining the emotional state of the at least some of the test subjects includes determining the emotional state of the identified subset of the test subjects.

26. The method of claim 25, comprising determining an emotional state for each of multiple subsets of the test subjects.

27. The method of claim 25, comprising identifying subjects belonging to each of the multiple subsets based on a demographic characteristic of each test subject, one or more received responses from each test subject, or both.

28. The method of claim 19, comprising presenting a report representative of the determined emotional state of the at least some of the test subjects.

* * * * *